(12) United States Patent
Higuchi

(10) Patent No.: US 7,903,847 B2
(45) Date of Patent: Mar. 8, 2011

(54) APPARATUS FOR INPUTTING BIOMETRICAL FEATURE

(75) Inventor: Teruyuki Higuchi, Tokyo (JP)

(73) Assignee: NEC Corporation, Tokyo (JP)

( * ) Notice: Subject to any disclaimer, the term of this patent is extended or adjusted under 35 U.S.C. 154(b) by 955 days.

(21) Appl. No.: 11/719,293

(22) PCT Filed: Nov. 15, 2005

(86) PCT No.: PCT/JP2005/020905
§ 371 (c)(1),
(2), (4) Date: May 14, 2007

(87) PCT Pub. No.: WO2006/051976
PCT Pub. Date: May 18, 2006

(65) Prior Publication Data
US 2009/0074263 A1   Mar. 19, 2009

(30) Foreign Application Priority Data

Nov. 15, 2004   (JP) .................................. 2004-330830

(51) Int. Cl.
*G06K 9/00* (2006.01)
(52) U.S. Cl. ......... 382/126; 382/115; 382/116; 382/124; 382/125; 382/127
(58) Field of Classification Search .................. 382/126, 382/124, 125, 127, 115, 116
See application file for complete search history.

(56) References Cited

U.S. PATENT DOCUMENTS

| 4,699,149 | A | 10/1987 | Rice |
| 6,381,347 | B1 | 4/2002 | Teng et al. |
| 6,785,407 | B1 * | 8/2004 | Tschudi et al. ............... 382/124 |
| 2001/0026632 | A1 | 10/2001 | Tamai |
| 2003/0063783 | A1 | 4/2003 | Higuchi |
| 2003/0161510 | A1 * | 8/2003 | Fujii ............................. 382/124 |
| 2004/0017891 | A1 | 1/2004 | Endo |
| 2005/0047632 | A1 | 3/2005 | Miura et al. |

FOREIGN PATENT DOCUMENTS

| JP | 04-190470 | 7/1992 |
| JP | 05-168610 | 7/1993 |
| JP | 08-154921 | 6/1996 |
| JP | 10-91769 | 4/1998 |
| JP | 10-143663 | 5/1998 |
| JP | 10-208022 | 8/1998 |
| JP | 10-222641 | 8/1998 |
| JP | 10-255050 A | 9/1998 |
| JP | 3045629 | 3/2000 |
| JP | 3150126 | 1/2001 |
| JP | 2001-92951 | 4/2001 |

(Continued)

*Primary Examiner* — Matt Bella
*Assistant Examiner* — Mike Rahmjoo
(74) *Attorney, Agent, or Firm* — Dickstein Shapiro LLP

(57) ABSTRACT

A biometrical feature inputting apparatus includes a 1-dimensional or quasi 1-dimensional image sensor. When a finger and the image sensor are relatively slid, a finger sliding guide keeps a finger and an effective pixel unit of the image sensor to a constant distance without any contact between them. An image processing section sequentially generates partial images by imaging emission light that is scattered inside the finger and then emitted from a skin surface of the finger by the image sensor during the relative motion of the finger and the image sensor and link the partial images to an image.

4 Claims, 19 Drawing Sheets

FOREIGN PATENT DOCUMENTS

| | | |
|---|---|---|
| JP | 2001-155137 | 6/2001 |
| JP | 2002-49913 | 2/2002 |
| JP | 2003-6627 | 1/2003 |
| JP | 2003-85538 | 3/2003 |
| JP | 2003-150943 | 5/2003 |
| JP | 2003-303178 | 10/2003 |
| JP | 2003-308516 A | 10/2003 |
| JP | 2004-234040 | 8/2004 |
| JP | 2005-174280 | 6/2005 |
| JP | 2005-182474 | 7/2005 |
| JP | 2005-242907 | 9/2005 |
| JP | 2006-72764 | 3/2006 |
| JP | 2006-98340 | 4/2006 |
| WO | WO-2004/026139 A1 | 4/2004 |

* cited by examiner

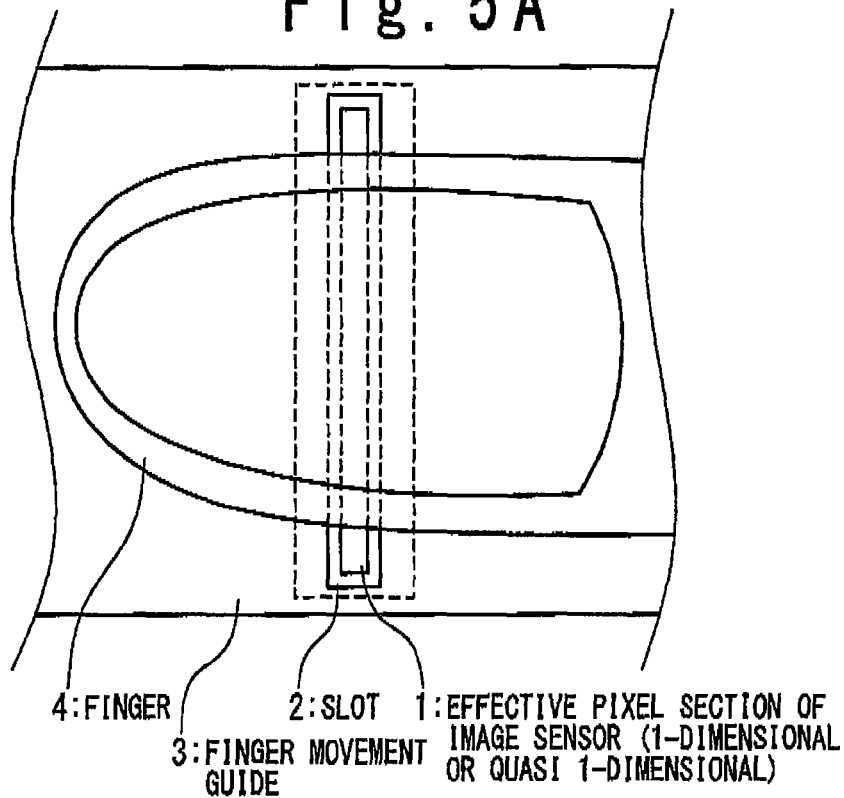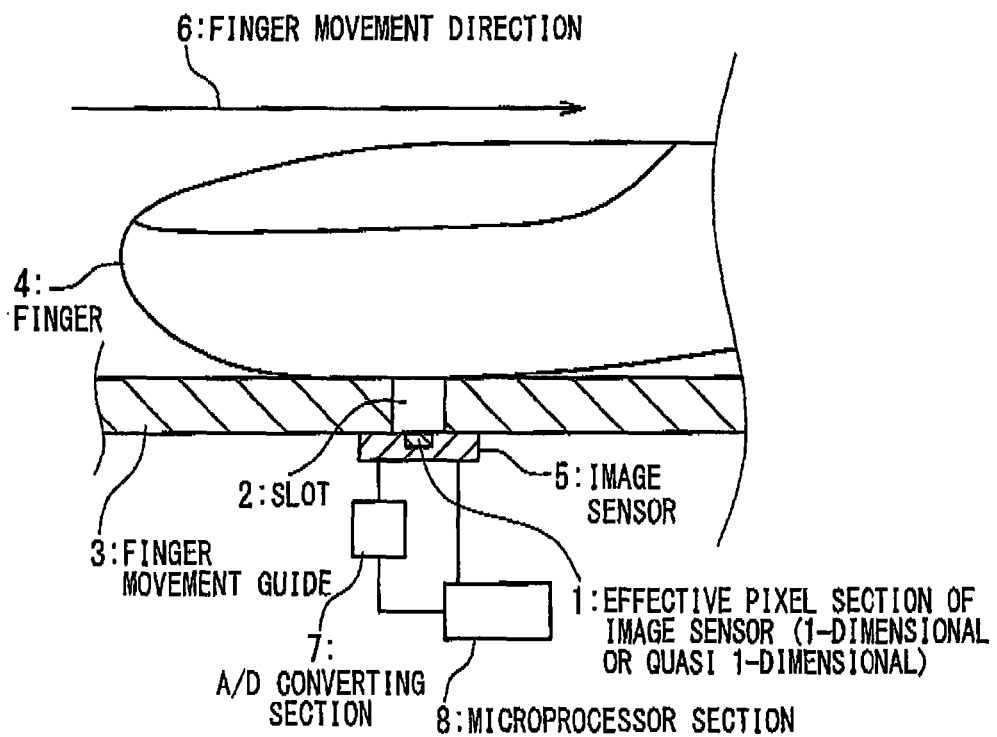

Fig. 23A　　　Fig. 23B
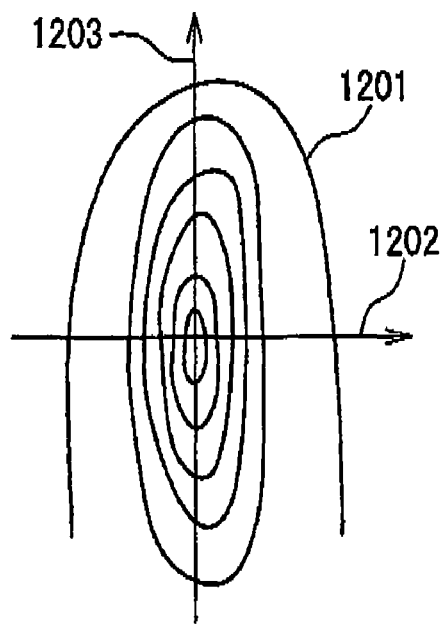 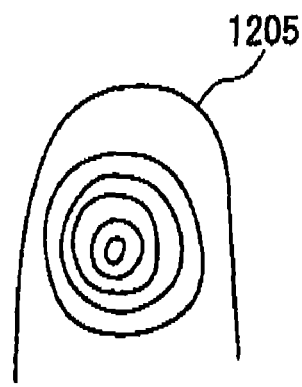
Fig. 24A　　　Fig. 24B
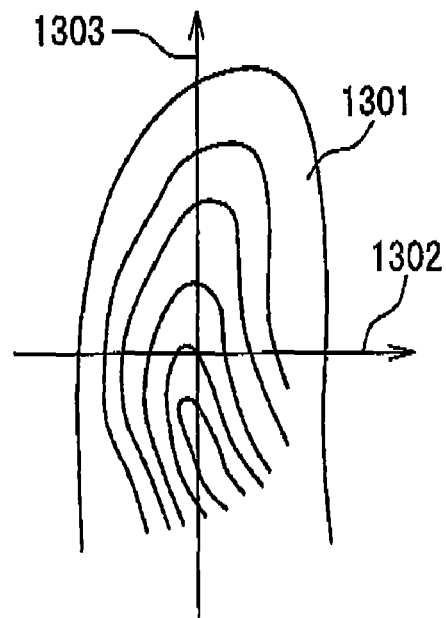 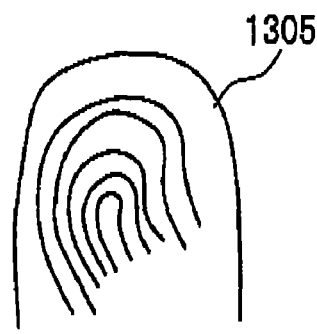

APPARATUS FOR INPUTTING BIOMETRICAL FEATURE

CROSS REFERENCE TO RELATED APPLICATIONS

This application is related to U.S. application Ser. Nos. 11/741,320 and 11/741,645, both filed on Apr. 27, 2007, and claims priority to PCT/JP2005/020905 filed on Nov. 15, 2005, which claims priority to Japanese application no. 2004-330830 filed on Nov. 15, 2004, the disclosure of which is incorporated by reference in its entirety.

TECHNICAL FIELD

The present invention relates to a biometrical feature inputting apparatus to authenticate a person.

BACKGROUND ART

In recent years, in accompaniment with advancement of an information system, the leakage of personal information and the spoofing of a different person in a transaction on a network have become problematic. In order to prevent these problems, an apparatus is developed that inputs features peculiar to a person and authenticates the person. Also, a smaller size and lower price of an information processing apparatus represented by a mobile phone has been advanced, and a biometrical feature inputting apparatus is also required to be miniaturized and cheapened. Moreover, the personal authentication based on the biometrical features is used for settlement of transaction by use of a credit card. For this reason, a higher precision of the biometrical feature input apparatus is required more and more, in order to surely authenticate the person under any situation.

Conventionally, this type of the biometrical feature input apparatus for personal authentication is represented by an apparatus for reading a fingerprint that is the pattern of a skin of a fingertip. The fingerprint is not same between all people and never changed in one's life. Especially, this is researched in police and justice fields and used for the personal authentication of a high precision.

For example, as described in U.S. Pat. No. 3,045,629 and U.S. Pat. No. 6,381,347, a method of using a total reflection critical angle of a fiber optic plate and a prism is widely used as a fingerprint input apparatus. The conventional fingerprint input apparatus that uses the total reflection critical angle of the prism will be described with reference to FIG. 1. The skin 104 of a finger is shown by enlarging the pattern of the skin. A lens 106 and a 2-dimensional image sensor 107 are arranged in a direction orthogonal to a prism plane 109 of a prism 105. A light beam 101 is inputted from a portion of the finger that is not in contact with the prism to a prism plane 108 having the refractive index more than 1.4 from the air layer having the refractive index of 1.0 into a prism plane 108. This is largely refracted and totally reflected on the prism plane 109, or does not arrive at the prism plane 109 and does not arrive at the 2-dimensional image sensor 107. On the other hand, the refractive index of fats and oils or water on the skin and the skin surface is close to that of a prism glass. Thus, a light beam 102 emitted from a portion of the finger with which the skin is in contact is inputted to the lens 106 without arriving at the total reflection angle on the prism plane 109, because the refractive angle of the prism plane 108 becomes small, and generates an image through the lens 106 and arrives at the two-dimensional image sensor 107. In this way, the fingerprint pattern is obtained depending on whether or not a concave/convex section pattern of the skin such as the fingerprint of the finger is brought into contact with the prism. However, this conventional fingerprint input apparatus uses an optical part that is expensive and large, which disturbed the miniaturization and lower price of the apparatus.

In order to attain the miniaturization of the fingerprint input apparatus, a technique is proposed that uses a quasi 1-dimensional sensor using a pressure, temperature and capacitance, and then links partial images of the fingerprint of the finger obtained when a finger is moved and a fingerprint image is re-assembled, and is disclosed in Japanese Laid Open Patent Application (JP-A-Heisei 10-91769 and JP-P2001-155137A). The technique that uses a 1-dimensional sensor and moves a read target and then reconfigures partial images is already known in a facsimile and a copier. However, this requires the special mechanism to obtain the speed in the direction in which the finger is moved. In order to omit a special mechanism, a technique proposed in Japanese Laid Open Patent Application (JP-A-Heisei 10-91769) reconfigures the partial images based on the similarity between the images on meta-1-dimensional several lines.

An image reconfiguration example of the fingerprint in this method will be described below with reference to FIGS. 2A and 2B. As an image of a finger 301, partial images I1 to In are obtained when the finger is moved. The similar partial images are removed from those partial images, and a reconfigured fingerprint image 302 is obtained. However, in this method, as shown in FIGS. 3A and 3B, when the finger is slowly moved with respect to the imaging speed of a sensor, the overlap becomes wide between the partial images adjacent to each other, and the judgment of the similarity becomes difficult. Also, an obtained fingerprint image 303 is longitudinally extended and distorted. Oppositely, if the finger is slid faster than the imaging speed, as shown in FIGS. 4A and 4B, the lost image appears between the partial images I1 to In, and longitudinally contracted and distorted such as a fingerprint image 304. In this way, this conventional example has a problem in which the fingerprint authentication, namely, the authentication based on the biometrical feature is hard to attain, if dermatitis cause the skin to be partially peeled, in addition to the foregoing problems.

Under such an environment, a non-contact fingerprint detection apparatus is proposed in, for example, Japanese Laid Open Patent Application (JP-P2003-85538A). According to this non-contact method, even in the finger that is hard to read because of difficulty in contact of the skin peeling portion in the method in which the foregoing contact is assumed, its image is obtained if a portion of the structure inside the skin resulting in a skin pattern is stored. Also, because of the non-contact, it is difficult to receive the influence of the state change on the skin surface such as a wet or dry state.

In this conventional example, a light is inputted to the finger and scattered inside the finger, and emission light is emitted from the finger to reflect the inner structure of the skin. In the thus-obtained fingerprint image, the concave section of the fingerprint becomes a bright region, and the convex section becomes a dark region, and the bright and dark image having the same shape as the fingerprint is obtained. In this way, in this conventional example, even when an epidermis horny layer is stripped and dropped due to the dermatitis, the fingerprint image is obtained independently of the wet or dry state of an epidermis if the structure of a cutis serving as a cutis pattern of the fingerprint is stored. However, in case of the fingerprint detecting apparatus described in Japanese Laid Open Patent Application (JP-P2003-85538A), unless a space is provided between the finger and an image forming system so as to accomplish the non-contact between them, an intended image cannot be obtained. Also, a frame for fixing the finger is required from the necessity of adjusting a focus, which disturbs the operability and the miniaturization of the apparatus. Also, the image forming optical system is required, which makes the apparatus larger. Also, the finger and the image forming system are separated, so that light emitted from the skin surface is scattered on the skin surface even if the inner structure of the finger causes the light quantity emitted from the skin surface to be changed. For this reason, the fingerprint image of excellent contrast cannot be obtained in the portion in which the skin is actually stripped, because of an adverse influence to the image forming system due to the separation.

For this reason, a reading apparatus that uses a physical absolute value and a change amount such as a light, an electric field, a pressure, a capacitance and a temperature, is variously developed. For example, a fingerprint input apparatus is proposed in Japanese patent No. 3150126 by the inventor of this application, in which a 2-dimensional image sensor is provided closely to the finger, and the scattered emission light from the finger is imaged through a transparent protection cover made of glass by the 2-dimensional image sensor, to obtain a fingerprint image in which the concave section of the fingerprint is a dark region and the convex section is a bright region. This conventional example is hard to receive the influence of the external environment such as the wet or dry state of the finger and the external disturbance light, as compared with the sensor that uses the pressure, the temperature, the capacitance and the total reflection critical angle, and attains the miniaturization and low price of the apparatus. However, this requires the large 2-dimensional image sensor, and although an optical system such as a lens is removed, the further miniaturization and lower price of the apparatus are obstructed. Also, as described in Japanese Laid Open Patent Application (JP-P2003-006627A) proposed by the inventor of this application, the image of high contrast can be obtained by optimally selecting the refractive index of the transparent protection cover.

Also, the fact that a fingerprint image obtained from a scattered emission light from a finger greatly depends on the boundary situation between its skin and a sensor protection film, is pointed out in Japanese Laid Open Patent Application (JP-P2003-006627A) proposed by the inventor of this application. On the other hand, the scattered emission light from the finger obviously reflects the structure inside the finger, because the light is once inputted into the finger. Thus, in the fingerprint input apparatus according to Japanese patent No. 3150126 proposed by the inventor of this application, a certain small fingerprint detecting apparatus is attained in which an optical image forming system is removed. Also, the inner structure of the skin of the finger is reflected even in the non-contact portion in which the skin is stripped, which is pointed out in Japanese Laid Open Patent Application (JP-P2003-85538A). However, when the refractive index of the transparent cover existing between the fingerprint and the 2-dimensional image sensor provided closely thereto is selected to increase the contrast between the bright region corresponding to the convex section of the fingerprint in contact with the transparent cover and the dark region corresponding to the concave that is not in contact, as described in Japanese Laid Open Patent Application (JP-P 2003-006627A), the influence of the reflection and refraction on the boundary becomes strong so that a light component reflecting the skin structure becomes small. As a result, it is difficult to obtain the contrast of the fingerprint image which reflects the skin structure originally appearing in the portion in which the skin is stripped. This problem is especially severe when a dynamic range of the image sensor cannot be widely set. When the non-contact state is kept, there is no influence on the boundary. However, it is impossible to keep the non-contact state in a constant distance from the finger having a curvature to the 2-dimensional image sensor, and it is also difficult to obtain the stable fingerprint image.

On the other hand, as the input apparatus of the biometrical feature existing on the finger, a technique for authenticating a blood vessel pattern on a finger base side below a first knuckle in addition to the fingerprint pattern is put to practical use in recent years. This technique uses the absorption of near-infrared light by blood and reads a thick blood vessel pattern such as vein. This is an application of the technique of an optical CT (Computer Tomography) earnestly researched in the 1980s, namely, the technique to perform a so-called computer tomography of a living body by using light harmless for the living body. When the near-infrared light is emitted from above the finger, the light that is passed through the finger and emitted from the cushion of the finger on the opposite side becomes dark due to the absorption of the near-infrared light by the blood in the blood vessel, and the blood vessel image is consequently obtained. For example, as disclosed in Japanese Laid Open Patent Application (JP-P2001-155137A), if this image can be read together with the fingerprint pattern, this serves as the supplement for the fingerprint information or becomes an effective information source on whether or not it is the living body, and this is effective as the judging method of a spurious finger.

However, the effective information amount of the blood vessel pattern is typically smaller than those of various fingerprints, and this is changed due to any trouble such as a nutrition state, a blood clot, and a blood pressure. As compared with the fingerprint which is mainly used in the police and justice fields because there is no same fingerprint and never changed in one's life and the research is already completed, that precision is not still checked, and remains as a future research subject. Also, similarly to the proposal (Japanese Laid Open Patent Application (JP-P2003-85538A)) of the non-contact fingerprint detection apparatus, a space is required between the fingerprint and the image forming system, and a frame for fixing the finger is required from the necessity of adjusting the focus, which obstructs the operability and the miniaturization of the apparatus. Also, only a capillary vessel exists in a fingertip, and the pattern of the capillary vessel cannot be read by the foregoing method. The readable vein blood vessel is located on the finger base side below the first knuckle. Thus, that portion must be read by a small optical system in addition to the fingerprint pattern of the fingertip above the first knuckle.

In relation to the foregoing explanation, a fingerprint detection method is disclosed in Japanese Laid Open Patent Application (JP-A-Heisei 5-168610) This fingerprint detection method of the conventional example is an optical fingerprint detecting method in which a light is emitted from a light source to a specimen including a potential fingerprint and calculates the obtained fingerprint image to detect the fingerprint. A surface temperature of the specimen is measured in advance and stored as a thermal image data, and the light of a wavelength in a region in which the absorption property is changed depending on the amount of water or organic substances included in the fingerprint component is emitted to the specimen for a certain time, and the emission light is then cut. The temperature of the specimen surface at that time is measured to obtain a thermal image data. The thermal image data prior to the light emission that is preliminarily measured and stored and the thermal image data after the light emission are converted into electronic signals, a difference in a 2-dimensional temperature distribution is calculated, and an image obtained as the calculated result is displayed, to specify the location of a fingerprint ridge section.

Also, a fingerprint information processing apparatus is disclosed in Japanese Laid Open Patent Application (JP-A-Heisei 10-143663). This fingerprint information processing apparatus of the conventional technique has a fingerprint image detector for detecting the fingerprint of a targeted person partially and optically. A relative position detector detects relative positions of a plurality of partial fingerprint images detected by the fingerprint image detector. An image synthesizer generates a synthesis fingerprint image by synthesizing the plurality of partial fingerprint images while compensating the mutual positional displacements between the plurality of partial fingerprint images in accordance with the relative position data detected by the relative position detector. A storage unit registers the data of the synthesis fingerprint image as a registration fingerprint image for individual identification information.

Also, a fingerprint authenticating apparatus is disclosed in Japanese Laid Open Patent Application (JP-P2002-49913A) In this fingerprint authenticating apparatus of the conventional example, a optical sensor region of an optical image sensor has an effective image region that a scattered light from inside a finger is converted into an image signal; and a black reference region that no reaction is taken for light. The black reference region may be connected with a silicon substrate that serve as a main body of the optical image sensor by a thermally conductive film, and this is formed by forming an optical light shielding film on a silicon dioxide film that covers the optical sensor region. A black reference region reader reads a dark current of a photo diode of the optical image sensor before and after the finger is placed on the optical image sensor, and a dark current comparator compares both current signals. When a difference of a predetermined value or more is detected from an image signal, a fingerprint checker acquires the image signal in the effective image region and checks and compares it with a fingerprint database. If the difference of the predetermined value or more is recognized as the comparison result of the image signal, a fingerprint determining unit determines the finger to be true, only when the feature is coincident with the fingerprint database as the result of the check.

DISCLOSURE OF INVENTION

It is therefore an object of the present invention to provide a biometrical feature inputting apparatus, which can stably input a biometrical feature such as a fingerprint of a finger by using a 1-dimensional or quasi 1-dimensional image sensor, and has a small size and a low price.

Another object of the present invention is to provide a biometrical feature inputting apparatus, which can input a blood vessel pattern of a finger together with a fingerprint pattern of the finger and has a small size and a low price.

Still another object of the present invention is to provide an electronic equipment which has a finger sliding guide to stably input a biometrical feature such as a fingerprint pattern of the finger by using a 1-dimensional or quasi 1-dimensional image sensor.

In an aspect of the present invention, the biometrical feature inputting apparatus includes a 1-dimensional or quasi 1-dimensional image sensor; a finger sliding guide that keeps a substantially constant distance without any contact between a finger and an effective pixel unit of the image sensor during a relative motion in which the finger and the image sensor are slid; and an image processing section for linking 1-dimensional or quasi 1-dimensional partial images obtained by imaging an emission light that is scattered inside the finger and then emitted from the skin surface of the finger.

In another aspect of the present invention, the biometrical feature inputting apparatus includes a 1-dimensional or quasi 1-dimensional image sensor; a finger sliding guide that keeps a substantially constant distance without any contact between a finger and an effective pixel unit of the image sensor during a relative motion in which the finger and the image sensor are slid; an upper light source for emitting a light for a blood vessel pattern to a rear of the finger; and an image processing section for linking 1-dimensional or quasi 1-dimensional partial images, which are obtained by alternately imaging as first partial images, an emission light that is scattered inside the finger and then emitted from a skin surface of the finger and as second partial images, an emission lights that is emitted on the skin surface of the finger after the light emitted from the upper light source is passed through the finger by using the image sensor during the relative motion, for each first partial image and for each second partial image, and then by extracting the blood vessel image that is a difference between the reconfigured first and second images from the partial images.

In the biometrical feature inputting apparatus, the finger sliding guide may have a gap immediately over the effective pixel unit of the image sensor. Preferably, the height of the gap is 10 µm or more and 200 µm or less, and the width parallel to the relative motion direction is the effective pixel length or more and 2.0 mm or less in the sub scanning direction of the image sensor. Also, an optically transmissible solid body may be inserted into the gap.

Also, the portion immediately over the effective pixel unit of the image sensor in the finger sliding guide may be formed of an optically transmissible solid. The height of the solid body is preferred to be 10 µm or more and 200 µm or less. Also, the refractive index of the solid is preferred to be more than 1.1. The refractive index of the solid is further preferred to be between 1.1 and 1.4. Also, the refractive index of the solid is preferred to be more than 2.0. The refractive index of the solid is further preferred to be between 2.0 and 5.0.

The biometrical feature inputting apparatus may further contain a low light source, which generates the scattered light inside the finger by emitting light to the cushion of the finger from the vicinity of a reading target portion through the image sensor.

Also, the biometrical feature inputting apparatus may further include a band pass filter for extracting an image component of a fingerprint pitch from an output image signal of the image sensor; and an automatic gain control circuit for amplifying the output of the band pass filter.

Also, in the biometrical feature inputting apparatus, the image processing section may contain a compensating unit for modifying the distortion of the link resultant image through the frequency analysis of a fingerprint portion.

Preferably, the first electronic equipment of the present invention has, immediately over the effective pixel unit of a 1-dimensional or quasi 1-dimensional image sensor, a gap in which a height is 10 µm or more and 200 µm or less and a width of a short side is an effective pixel length or more and 2.0 mm or less in the sub scanning direction of the image sensor, and includes a finger sliding guide that keeps a substantially constant distance without any contact between the finger and the effective pixel unit of the image sensor, during the relative motion in which the finger and the image sensor are slid together.

In the electronic equipment of the present invention, an optically transmissible solid is inserted into the gap.

In the present invention, during the relative motion in which the finger and the 1-dimensional or quasi 1-dimensional image sensor are slid, as well as the finger sliding guide prevents a contact between the finger and the effective pixel unit of the image sensor, a distance between them is kept substantially constant, which prevents an image from being unclear because of the excessively long distance between the finger and the effective pixel unit or prevents the image from being distorted because of a variation in the distance. Also, the emission light that is emitted from the skin surface of the finger after being scattered inside the finger can be stably imaged by the image sensor during the relative motion. Moreover, it is possible to improve the precision of the image of the entire finger that is generated by linking the imaged 1-dimensional or quasi 1-dimensional partial images.

BRIEF DESCRIPTION OF DRAWINGS

FIGS. 5A and 5B are a top view and a side sectional view of the biometrical feature inputting apparatus according to a first embodiment of the present invention, respectively;

FIGS. 23A and 23B are diagrams showing a image compensating method for a spiral fingerprint in the biometrical feature inputting apparatus according to the sixth embodiment of the present invention;

FIGS. 24A and 24B are diagrams showing a image compensating method for a hoof fingerprint in the biometrical feature inputting apparatus according to the sixth embodiment of the present invention;

BEST MODE FOR CARRYING OUT THE INVENTION

Figure 1:
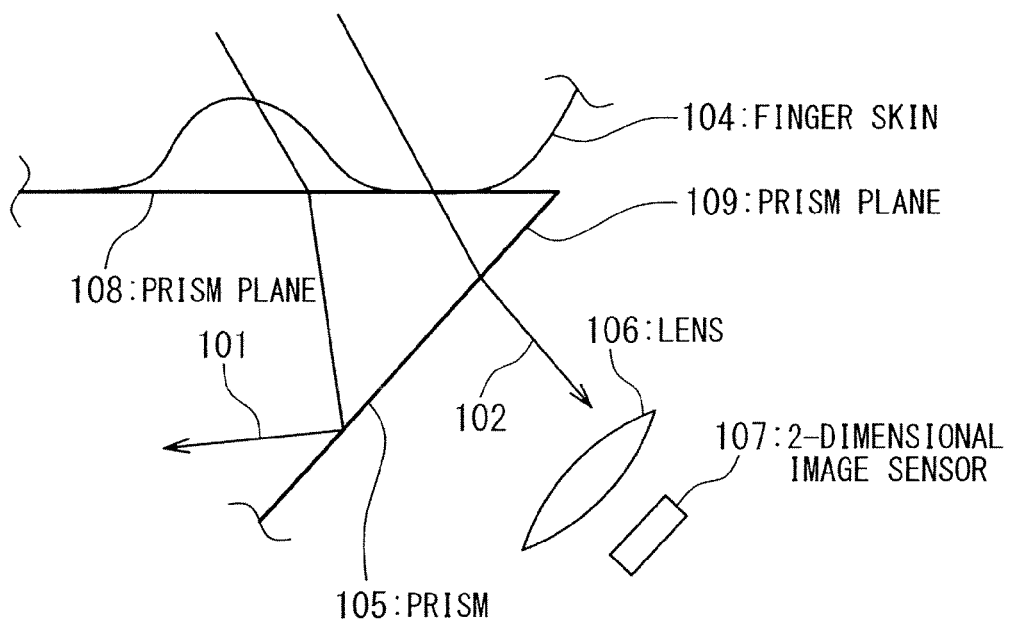
FIG. 1 is a diagram showing a principle of a conventional optical prism method in which contact is assumed.

Hereinafter, the biometrical feature inputting apparatus according to the present invention will be described in detail with reference to the attached drawings.

First Embodiment

FIGS. 5A and 5B are views showing the biometrical feature inputting apparatus according to the first embodiment of the present invention. With reference to FIGS. 5A and 5B, the biometrical feature inputting apparatus according to the first embodiment includes a 1-dimensional or quasi 1-dimensional image sensor 5, a finger sliding guide 3 provided in such a manner that a gap 2 is located immediately above an effective pixel unit 1 on this image sensor 5, an A/D converter 7 for converting an analog output signal of the image sensor 5 into a digital signal, and a microprocessor 8 for controlling the imaging (operation) timing of the image sensor 5 and performing an imaging process on the digital signal outputted from the A/D converter 7.

The 1-dimensional image sensor 5 is an image sensor for one line, and the quasi 1-dimensional image sensor 5 is a rectangular image sensor of about 2 to 20 lines. When a ridge section interval in the fingerprint pattern is about 0.2 to 0.5 mm in case of an adult, and it is about 0.1 mm or less in case of a child and a lady, the fingerprint as the biometrical feature of the finger can be read. A pitch between light receiving elements is desired to be about 20 to 50 µm. When the width and roundness of the finger are considered and the lateral width of about 15 mm is assumed to be a contact effective portion, and the 12 lines of the sensors of 512 dots per one line in the interval of 29.6 µm are arranged to form the quasi 1-dimensional image sensor, a rectangular image of 15.15 mm in a lateral direction and 0.35 mm in a longitudinal direction is obtained one time. The image sensor 5 can be formed by using a CMOS, CCD and TFT technique, and this density and size can be sufficiently produced by use of a current integrated circuit technique. The necessary sufficient sensitivity can be obtained by considering the fact that the image sensor actually used in a video camera is 10 μm or less.

The finger sliding guide 3 is placed between a finger 4 and the image sensor 5 so that a predetermined constant distance is kept without any contact between the finger 4 and the effective pixel unit 1 of the image sensor 5, when the fingerprint pattern is imaged while the finger 4 and the image sensor 5 are relatively moved. In the first embodiment, the finger sliding guide 3 is made of opaque material, and attached to a housing (not shown) dedicated to the biometrical feature inputting apparatus or attached to the housing of an electronic equipment such as a mobile phone and a personal computer. The finger sliding guide 3 forms a part of the housing of the electronic equipment. Also, the shape of the gap 2 formed in the finger sliding guide 3 is rectangular when being viewed immediately over it. Its long side has a size equal to or longer than a long side of the effective pixel unit 1 in a main scanning direction at least so that the light is sufficiently inputted to the effective pixel unit 1 of the image sensor 5. Also, its short side has a size equal to or longer than a short side of the effective pixel unit 1 in a sub scanning direction at least so that the light is similarly sufficiently inputted to the effective pixel unit 1. If the gap 2 is too large, the skin of the finger 4 is brought into direct contact with the effective pixel unit 1, when the fingerprint pattern is imaged. Thus, the short side size is 2.0 mm or less, preferably, 1.0 mm or less. Also, the size of the gap 2 in the height (depth) direction is in a range of 10 μm and 200 μm, preferably, a range of 20 μm and 80 μm, since the skin of the finger 4 is brought into direct contact with the effective pixel unit 1 if case of the imaging of the fingerprint pattern if the gap 2 is too small, and since a distance between the skin of the finger 4 and the effective pixel unit 1 is excessively separated so that the image is severely made unclear, if the gap 2 is too large. The A/D converter 7 converts an analog output signal from the image sensor 5 into a digital signal and outputs to the microprocessor 8. The microprocessor 8 receives the digital signal from the A/D converter 7 and performs a suitable imaging process.

Figure 6:
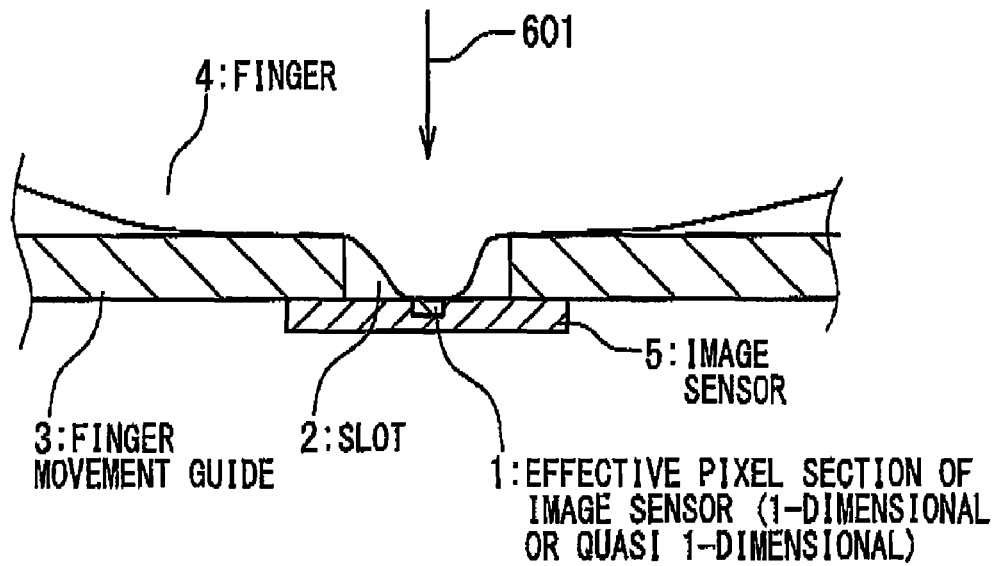
FIG. 6 is a diagram showing a situation in which a finger is pushed against a gap of a finger sliding guide in the biometrical feature inputting apparatus according to the first embodiment of the present invention.
Figure 7:
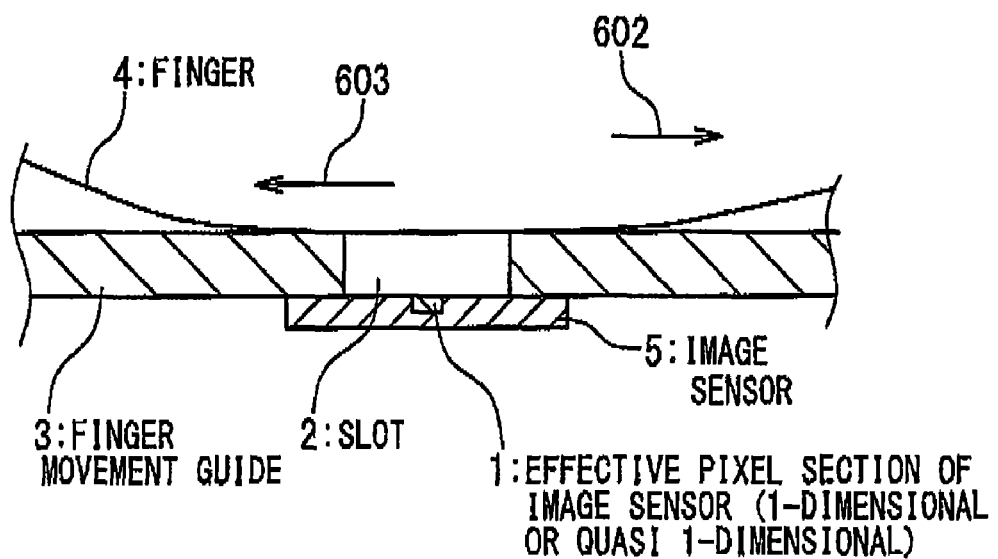
FIG. 7 is a diagram showing a situation in which the finger is moved along the finger sliding guide of the biometrical feature inputting apparatus according to the first embodiment of the present invention.

When the biometrical feature inputting apparatus in the first embodiment is used to read the fingerprint pattern of the finger 4, the vicinity of the first knuckle of the finger 4 is put near the gap 2 of the finger sliding guide 3, and then the finger 4 is pulled to the direction of an arrow 6 in FIG. 5B. The skin of the finger 4 is elastic. Thus, as shown in FIG. 6, when the finger 4 is pushed against the direction of an arrow 601, even in the gap 2 having the height and width in which the finger 4 is brought into contact with the effective pixel unit 1 of the image sensor 5. Also, when the cushion of the finger 4 is used to lightly trace the gap 2 as mentioned above, a force 603 in a direction opposite to a pull direction 602 is applied to the skin surface of the finger 4, as shown in FIG. 7. Therefore, under the situation that the finger 4 is never brought into contact with the effective pixel unit 1, the distance between the skin of the finger 4 and the effective pixel unit 1 is always kept constant during the movement of the finger 4.

Figure 8:
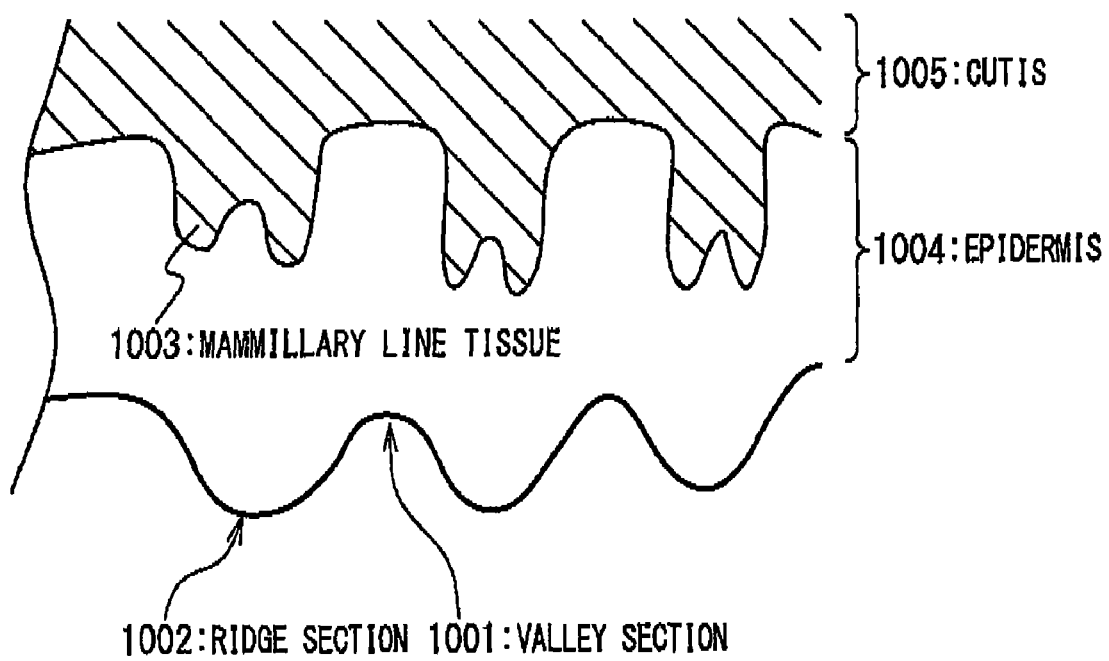
FIG. 8 is a diagram showing an inner structure of a skin of the finger.

While this finger 4 is moved, the image is generated by sensing the emission light that is emitted from the skin surface of the finger 4 after being scattered inside the finger 4, by the image sensor 5. Here, the light is emitted from the skin surface of the finger 4 after being scattered inside the finger 4 and generates a shadow in accordance with the inner structure of the finger as shown in FIG. 8. The skin tissue inside an epidermis 1004 has a cutis 1005, and there is a mammillae tissue 1003 below a ridge section 1002 that is the convex (ridge) section of the fingerprint pattern. The cutis 1005 including the mammillae tissue includes much water and oil components, as compared with the epidermis 1004, and a difference in a refractive index is generated. Thus, with this mammillae tissue protruding from the fingerprint ridge section, the light emitted from a valley section 1001 as the convex section of the fingerprint is considered to be reduced in the ridge section 1002. For this reason, among the light receiving elements arrayed in the effective pixel unit 1 of the image sensor 5, the input emission light becomes small in the light receiving element close to the ridge section 1002 at the timing of the imaging, as compared with the light receiving elements close to the valley section 1001. Then, a partial image is obtained in which the valley section 1001 is the bright region and the ridge section 1002 is the dark region.

Figures 2A, 2B:
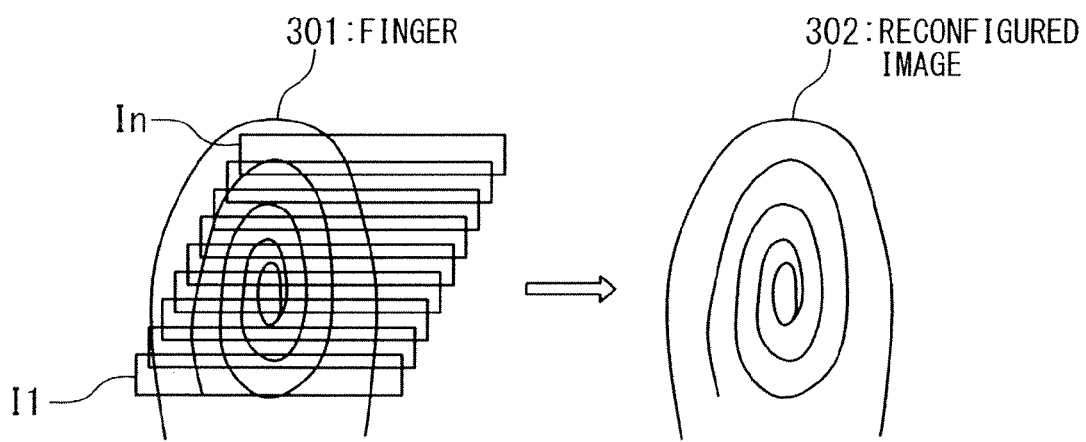
FIGS. 2A and 2B are diagrams showing a conventional image reconfiguration method.
Figure 3A:
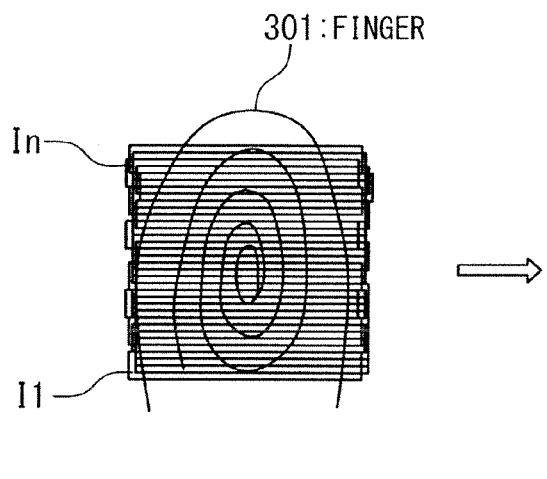
FIGS. 3A and 3B are diagrams showing a problem when a finger is slowly moved in the conventional image reconfiguration method.
Figure 3B:
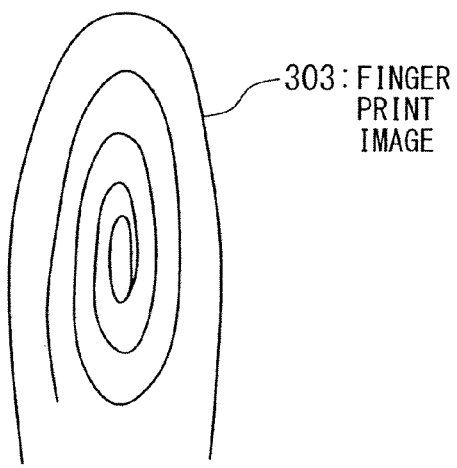
Figure 4A:
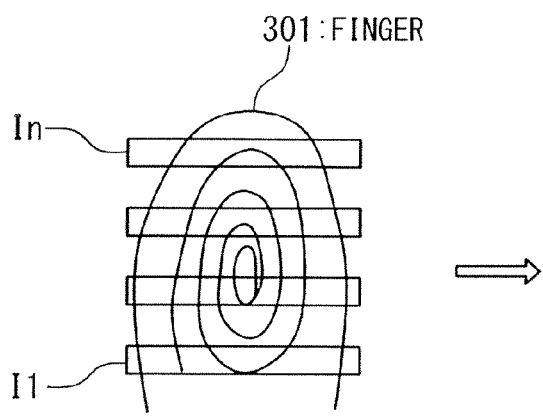
FIGS. 4A and 4B are diagrams showing a problem when the finger is quickly moved in the conventional image reconfiguration method.
Figure 4B:
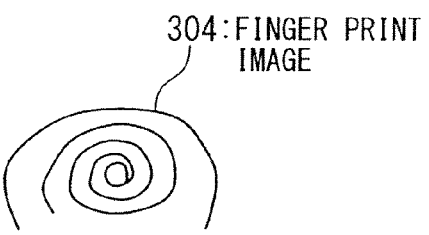
Figure 9:
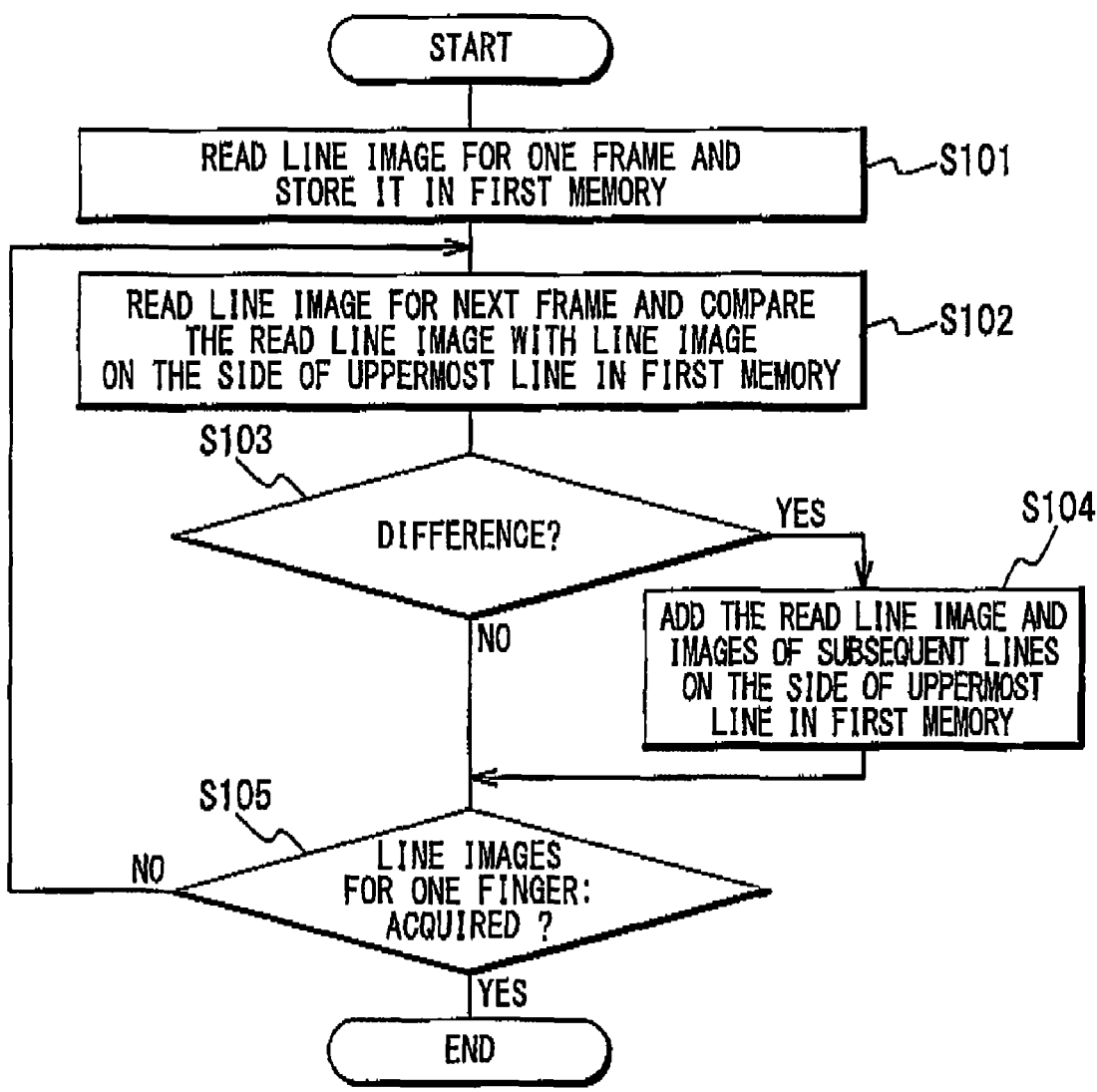
FIG. 9 is a flowchart showing a process example of a microprocessor in the biometrical feature inputting apparatus according to the first embodiment of the present invention.

In this way, an analog signal corresponding to the 1-dimensional or quasi 1-dimensional partial image obtained at each proper timing is converted into a digital signal by the A/D converter 7 and supplied to the microprocessor 8. The microprocessor 8 links the partial images sequentially and reconfigures an image of the entire skin pattern of the finger 4. A process for linking the partial images is executed by this microprocessor 8, to determine the similarity between the partial images, similarly to the method basically described in FIG. 2A. FIG. 9 shows one example of the process.

At first, a partial image for one frame of the image sensor 5 is read and writes into a bottom portion of a first memory (not shown) (Step S101). Here, the partial images for one frame imply an image for several lines, when the image sensor 5 is a quasi 1-dimensional image sensor for all the several lines, and imply an image for one line when the image sensor 5 is a 1-dimensional image sensor composed of one line.

Next, a partial image for one frame of the image sensor 5 is read and compares with the partial image stored in the first memory in units of lines from the top line (Step S102). If any one of the lines of the currently read partial image is different from any one of the lines of the partial image stored in the first memory through the above comparison, the lines of the currently read partial image which are above from the line having difference are additionally stored in lines on the top line of the partial image stored in the first memory. For example, in case that the image sensor 5 is composed of 12 lines, when the last 3 lines among the 12 lines read at this time are equal to the 3 lines on the highest side of the partial images stored in the first memory, and a portion between the first line and the ninth line corresponding to the fourth line from the bottom is different, the image portion between the first line and the ninth line is added on the highest line of the first memory. The processes at the above steps S102 to S104 are repeated until the image data corresponding to one finger is obtained (Step S105).

According to the first embodiment, since the 1-dimensional or quasi 1-dimensional image sensor 5 is used without any unnecessary optical part, the image of the skin pattern in which the inner structure of the finger 4 is directly reflected can be stably read without any influence such as the wet or dry state of the finger 4, and the apparatus can be simplified and miniaturized. This reason is as follows. That is, as the image sensor 5, the 1-dimensional or quasi 1-dimensional image sensor that has the small size and the low price is used, and the finger sliding guide 3 is contained in order to keep the substantially constant distance without any contact between the finger 4 and the effective pixel unit 1 of the image sensor 5 during the relative motion, and the image resulting from the emission lights that are emitted from the skin surface of the finger 4 after being scattered inside the finger 4 is directly imaged by the image sensor 5 during the relative motion, and the obtained 1-dimensional or quasi 1-dimensional partial images are linked by the imaging process of the microprocessor 8, and the pattern image of the finger is consequently reconfigured.

Also, even in the skin peeling portion in which the excellent contrast cannot be obtained because of the phenomenon in which the light may be spread on the skin surface and then spread through a lens and an optical path when the contracted optical system as disclosed in Japanese Laid Open Patent Application (JP-P2003-85538A) is used, the pattern having the excellent contrast in which the structure inside the finger is reflected is obtained according to the first embodiment. This is because in the first embodiment, since the light is directly inputted from the finger to the image sensor 5 in the distance close to the finger 4, the components which are spread on the skin surface and mixed to each other become small.

Second Embodiment

Figure 10A:
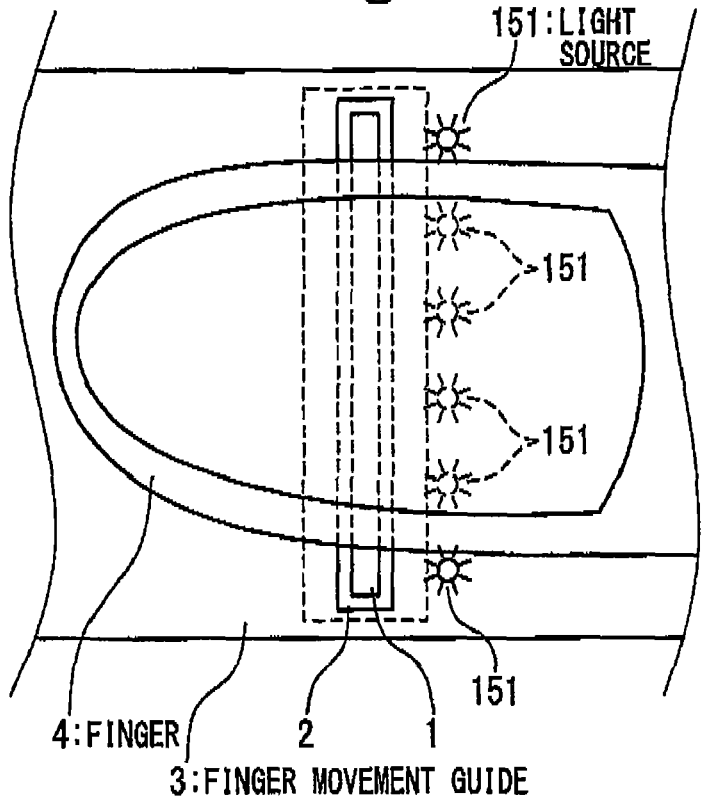
FIGS. 10A and 10B are a top view and a side sectional view of the biometrical feature inputting apparatus according to a second embodiment of the present invention.
Figure 10B:
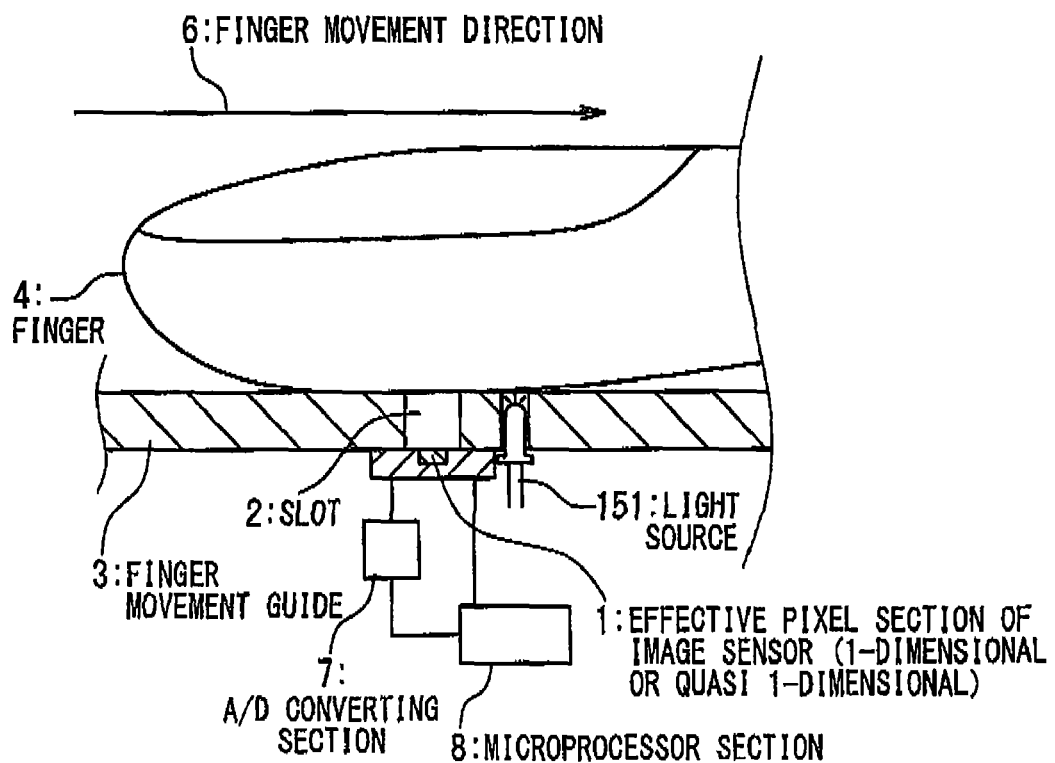

With reference to FIGS. 10A and 10B, the biometrical feature inputting apparatus according to the second embodiment of the present invention differs from the first embodiment shown in FIGS. 5A and 5B, in that a light source of a plurality of light emitting devices is placed on the finger sliding guide 3, and the configurations other than it are same as those of the first embodiment.

The light emitting devices of the light source 151 are arranged in one line along the long side near the gap 2 of the finger sliding guide 3. When the finger 4 moving in the direction shown by the arrow 6 on the finger sliding guide 3 to image the fingerprint pattern, the finger 4 is illuminated from its finger cushion side (the side of the finger sliding guide 3), to generate the scattered light inside the finger. The reason why the light emitting devices are arrayed on the side on which the finger 4 is pulled with respect to the gap 2 as a center is to make it possible to sufficiently generate the scattered light inside the fingertip even in the situation that the fingertip arrives at the vicinity of the gap 2.

As for the light emitted from the skin surface after being scattered inside the finger, the skin pattern can be read by simply using the peripheral light. Moreover, when the light source 151 is arranged in parallel and close to the 1-dimensional or quasi 1-dimensional image sensor 5 in the direction in which the finger is pulled, the lights from the light emitting devices of the light source 151 are scattered inside the finger, and the optical components in the light source direction are strongly emitted. This manner will be described below with reference to FIG. 11.

Figure 11:
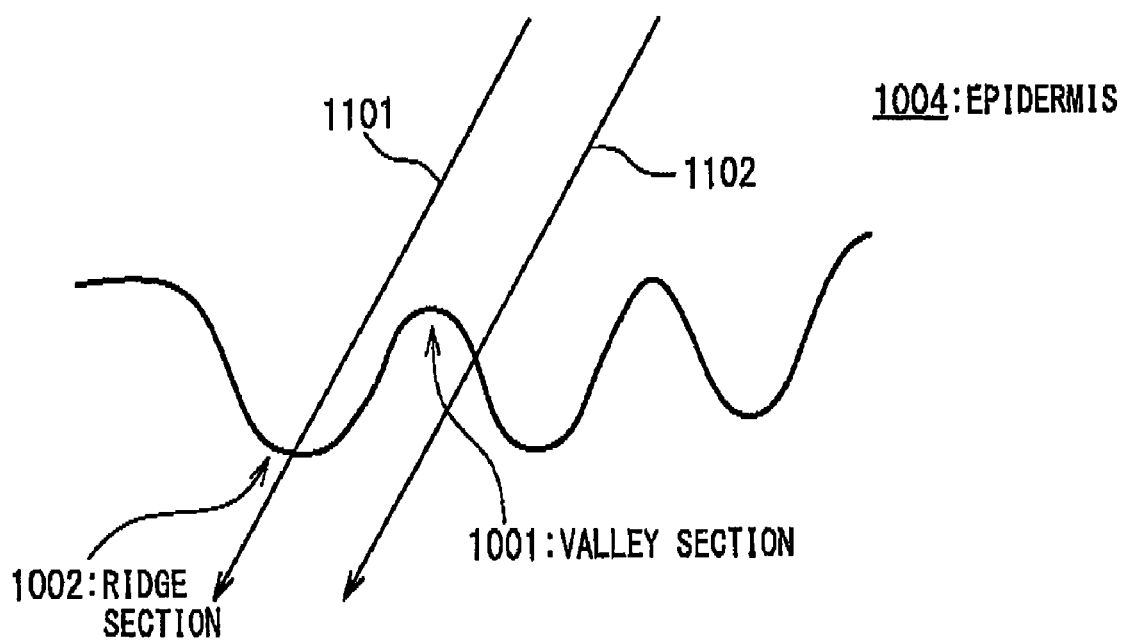
FIG. 11 is a diagram showing an operation of a light source of the biometrical feature inputting apparatus according to the second embodiment of the present invention.
Figure 12:
FIG. 12 is a diagram showing a fingerprint image example read by the biometrical feature inputting apparatus according to the second embodiment of the present invention.
Figure 13:
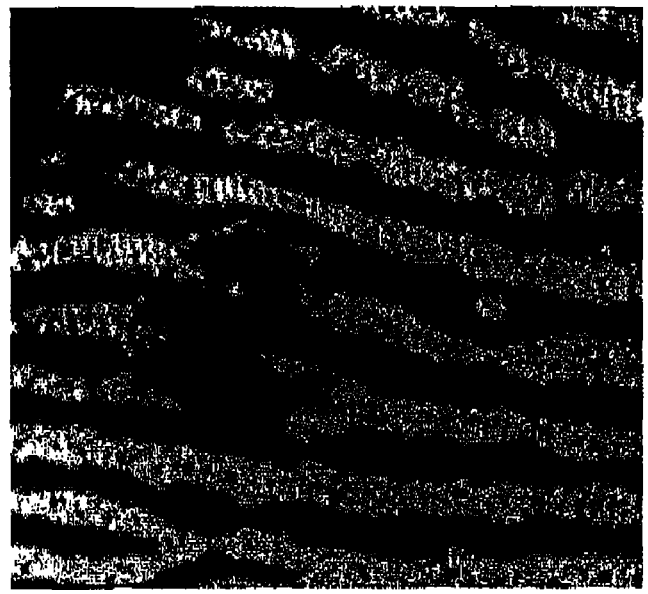
FIG. 13 is a diagram showing a fingerprint image example inputted by a fingerprint input apparatus that uses a conventional total reflection critical angle.

With reference to FIG. 11, of the scattered light components having intensity biased into the light source direction, the light component passing near the ridge section 1002 in a direction shown by an arrow 1101 is considered to be darker, because the distance in which the light passes through the cutis 1004 is longer. Oppositely, the light component passing near the fingerprint valley section 1001 in a direction shown by an arrow 1102 is considered to be brighter because the distance in which the light component passes through the cutis 1004 is shorter. Thus, the contrast is increased depending on the difference of the distance. Although the actual detailed mechanism is unknown, FIG. 12 shows the experiment result as an image example. Also, as a reference, FIG. 13 shows an image when the same portion of the same finger is read by the method that uses the total reflection critical angle, among the conventional methods in which the contacts are assumed.

In FIG. 12, there is the light source on the low portion side of FIG. 12, and is provided on the side in which the finger is pulled. The fingerprint ridge section having a longer emission distance becomes dark, and the front side of the valley section becomes bright. In particular, the light source side of the fingerprint ridge section becomes darker, and the contrast is increased. This portion is considered to overlap with the attenuation effect of the scattered light inside the skin of the finger, which results from the mammillae tissue 1003. Also, there is a part in which the pattern is lost around the image center of FIG. 13, and this corresponds to the portion in which the skin is stripped. The pattern appears for the same portion in FIG. 11, and the image of the skin peeling portion that has been conventionally lost is also obtained at the high contrast.

It should be noted that in the second embodiment, the light source 151 is arranged on the side in which the finger 4 is pulled from the gap 2. However, the light source 151 may be arranged on the opposite side with respect to the gap 2, or the light source 151 may be arrayed in the vicinities on both sides of the gap 2.

Third Embodiment

Figure 14:
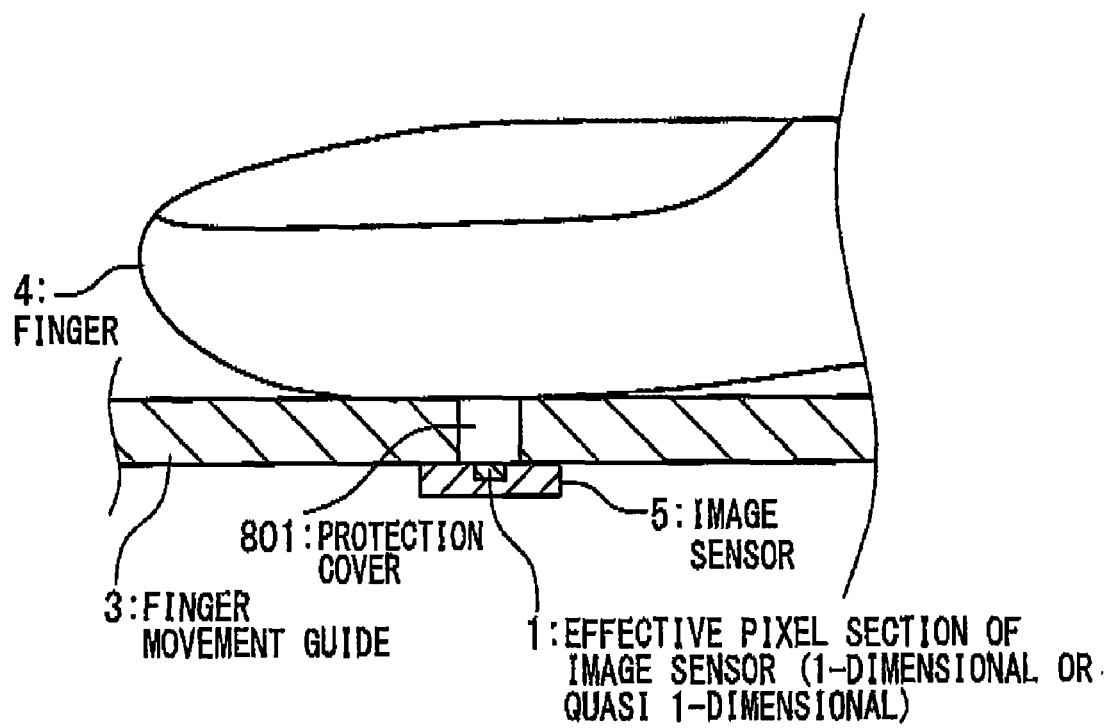
FIG. 14 is a laterally sectional view of the biometrical feature inputting apparatus according to a third embodiment of the present invention.

With reference to FIG. 14, the biometrical feature inputting apparatus according to the third embodiment of the present invention differs from the first embodiment shown in FIG. 1, in that a protection cover 801 made of optically transmissible solid is inserted into the gap 2 of the finger sliding guide 3, and the components other than it are same as those of the first embodiment.

Figure 15A:
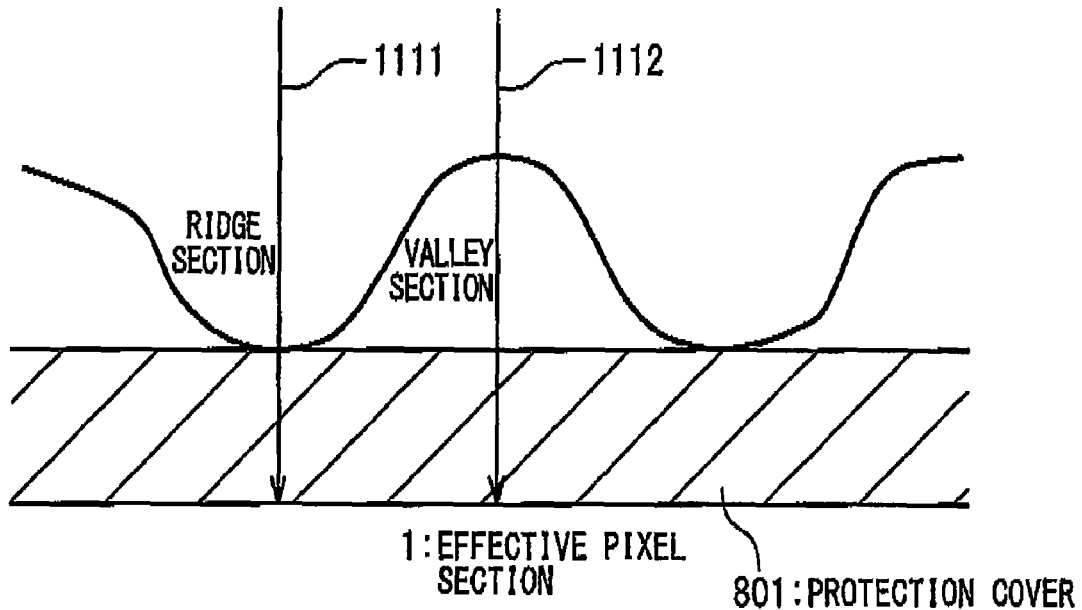
FIGS. 15A and 15B are diagrams sowing an operation of the biometrical feature inputting apparatus according to the third embodiment of the present invention.

The bottom plane of the protection cover 801 is in substantial contact with the effective pixel unit 1 of the image sensor 5, and its top plane is the substantially same plane as the top plane of the finger sliding guide 3. Thus, in order to read the fingerprint pattern of the finger 4, when the vicinity of the first knuckle of the finger 4 is put near the protection cover 801 embedded in the gap 2 of the finger sliding guide 3 and then the finger 4 is pulled so as to trace the protection cover 801, a part of the skin of the finger 4 is always in contact with the protection cover. Thus, among the light components that are emitted from the skin surface of the finger after being scattered inside the finger, the light component emitted from the fingerprint ridge section in contact with the protection cover is directly inputted to the protection cover 801, as shown by a numeral 1111 of FIG. 15A. This is propagated through the protection cover 801 and arrives at the effective pixel unit 1 of the image sensor 5. Also, the light component emitted from the fingerprint valley section that is not in contact with the protection cover 801 is once inputted to an air layer as shown by a numeral 1112 and propagated through the air layer and then inputted to the protection cover 801. After that, the light component is propagated through the protection cover 801, similarly to the light reflected from the fingerprint ridge section and arrives at the effective pixel unit 1 of the image sensor 5.

Figure 15B:
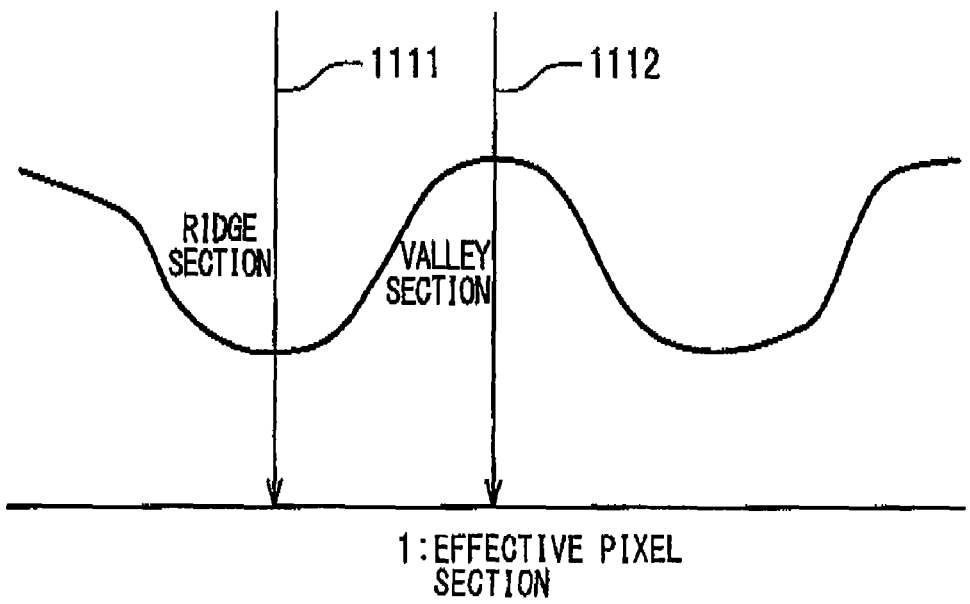

On the contrary, in case of the first embodiment that does not contain the protection cover 801 shown in FIG. 15B, the light components that are emitted from the skin surface of the finger after being scattered inside the finger are once inputted to the air layer and propagated through the air layer and then arrive at the effective pixel unit 1, as shown by the numerals 1111 and 1112 of FIG. 15B, irrespectively of the fingerprint ridge section and the fingerprint valley section. As a result, as described in the first embodiment, the ridge section is detected as the dark region, and the valley section is detected as the bright region by the image sensor 5. On the contrary, in case of the interposition of the protection cover 801 shown in FIG. 15A, if a refractive index of the protection cover 801 is similar to the same value of "1" as the air, this is equivalent to FIG. 15B in which the protection cover 801 does not exist. Thus, the ridge section is detected as the dark region, and the valley section is detected as the bright region by the image sensor 5. However, if the value of the refractive index of the protection cover 801 becomes greater, the ridge section is detected as the bright region, and the valley section is detected as the dark region by the image sensor 5. This is estimated from the following facts that, if the refractive index of the protection cover 801 is greater, the refractive index difference between the finger 4 and the air and the refractive index difference between the air and the protection cover 801 are greater than the refractive index difference between the finger 4 and the protection cover 801. Also, until the light component 1111 emitted from the ridge section in FIG. 15A arrives at the effective pixel unit 1, the light component passes through one boundary (the boundary between the finger and the protection cover) in which the refractive index difference is small. On the other hand, since the light component 1112 emitted from the valley section passes through the two boundaries (the boundary between the finger and the air and the boundary between the air and the protection cover) in which the refractive index difference is great, when the light component is emitted from the skin surface. Thus, the emission light from the valley section is stronger in intensity than the light component from the ridge section. However, when the light component arrives at the effective pixel unit 1, the light component sent from the ridge section becomes relatively stronger in intensity than the light component from the valley section. In fact, in the fingerprint input apparatus noted in the U.S. Pat. No. 3,150,126 that carries out the imaging by using the two-dimensional image sensor in which the scattered emission light from the finger is made close to the finger through the transparent protection cover made of glass, the fingerprint pattern is obtained in which the valley section of the fingerprint serves as the dark region and the ridge section serves as the bright region.

For this reason, when the refractive index of the protection cover 801 has a certain value, the contrast between the ridge section and the valley section becomes 0. In this description, the value of the above-mentioned refractive index is referred to as a singular point, and the protection cover 801 is made of optically transmissible solid having the refractive index of a value other than the values of the singular point vicinity. The refractive index of the protection cover 801 will be considered below.

Figure 16:
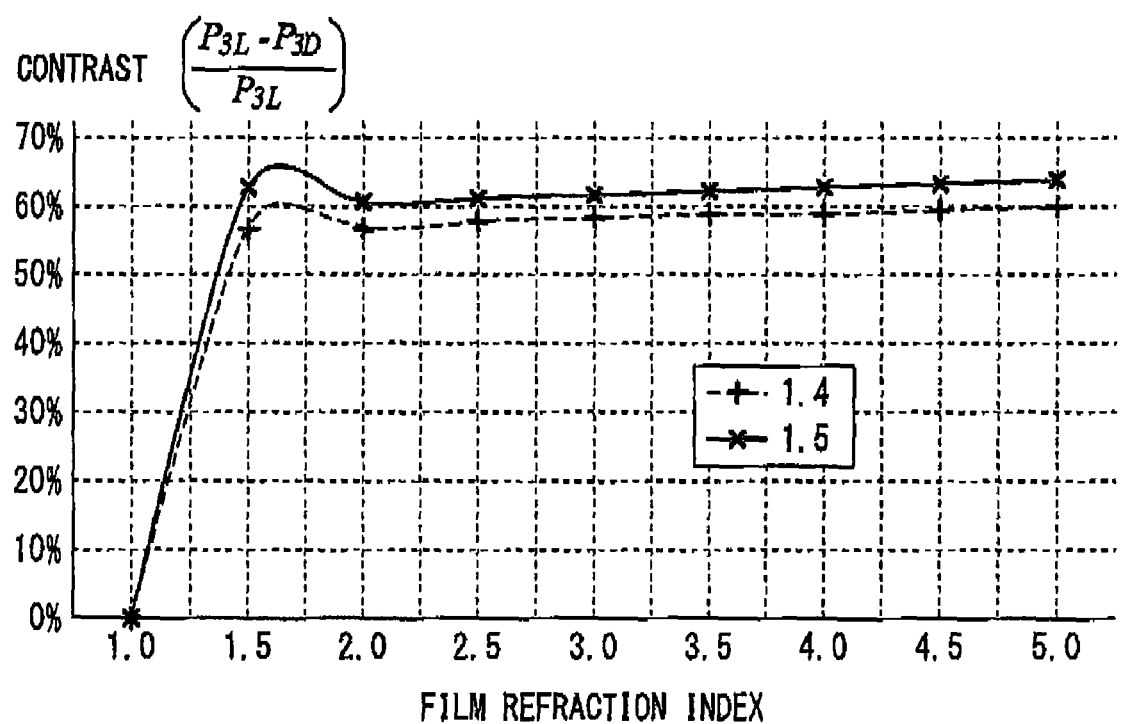
FIG. 16 is a graph showing a relation between a contrast and a refractive index of a transparent solid film that exists between a finger and a two-dimensional image sensor.

In Japanese Laid Open Patent Application (IP-P2003-006627A) as the proposal by the inventor of the present application, the relation between the refractive index and contrast of the transparent solid film located between the two-dimensional image sensor and the finger is analyzed. According to it, the relation as shown in FIG. 16 is derived. In FIG. 16, the vertical axis indicates the contrast that is calculated from (P3L−P3D)/P3L when the power of the light inputted to the transparent solid film immediately under the fingerprint ridge section is defined as P3L and the power of the light inputted to the transparent solid film immediately under the fingerprint ridge section is defined as P3D. The horizontal axis indicates the refractive index of the transparent solid film. Also, a line connecting the points of + marks is defined when the refractive index of the finger is assumed to be 1.4, and a line connecting the points of x marks is defined when the refractive index of the finger is assumed to be 1.5. However, the graph of FIG. 16 is determined by calculating only the effect resulting from the difference of the refractive index on the boundary between the skin of the finger, the air and the transparent solid film, and this differs from the effect resulting from the structure inside the skin of the finger.

With reference to FIG. 16, when the refractive index of the transparent solid film is 1.0 which is equal to that of the air, the contrast is 0%. This is because in the graph of FIG. 16, the power of the light sent to the ridge section from inside of the skin is assumed to be equal to the power of the light sent to the valley section. Originally, when the refractive index is 1.0, the same contrast as the first embodiment is obtained. In FIG. 16, that contrast value becomes minus. When the contrast obtained in the first embodiment is assumed to be C %, the value of the refractive index in which the contrast becomes C % in the graph of FIG. 16 serves as the singular point. Typically, because of C≈10, the singular point=1.1, and in the protection cover 801 whose refractive index is 1.1, the contrast between the valley section and the ridge section is 0. Thus, the refractive index of the protection cover 801 is required to be between 1.0 and 1.1 or greater than 1.1. The optically transmissible solid having the refractive index less than 1.1 does not substantially exist. Thus, the protection cover 801 may be formed of the optically transmissible solid having the refractive index that is substantially greater than 1.1.

On the other hand, with reference to FIG. 16, the contrast is especially high in the refractive index of the transparent solid film between 1.4 and 2.0. When the entire portion in which the skin is stripped is not in contact with the transparent solid film, the entire portion does not have the same contrast, but the pattern in which the structure inside the finger is reflected is generated as mentioned above. For this reason, if the contrast between the ridge section that contacts with the transparent solid film and the valley section that does not contact is abnormally high as compared with the contrast of the pattern, it is difficult to detect the pattern of the portion in which the skin is stripped when the dynamic range of the sensor is not wide. Therefore, the refractive index in the range between 1.4 and 2.0 in which the contrast is especially high in FIG. 16 is not suitable for the protection cover 801.

Moreover, as analyzed in Japanese Laid Open Patent Application (JP-P2003-006627A) as the proposal by the inventor of this application, when the refractive index of the transparent solid film becomes greater, the brightness is reduced even if the contrast appears. The S/N ratio is reduced due to noise caused by the external disturbance light and noise generated in the circuit. Therefore, a probability becomes higher that the identification between the fingerprint ridge section and the fingerprint valley section becomes inaccurate. Thus, the upper limit value of the refractive index is desired to be about 5.0. As the result of the above-mentioned considerations, the refractive index of the protection cover 801 is desired to be between 1.1 and 1.4 or between 2.0 and 5.0.

As the solid suitable for the protection cover 801 while having the refractive index less than 1.4, there is a glass whose main component is $BeF_3$ (beryllium fluoride). As the solid that is suitable for the protection cover 801 while having the refractive index greater than 2.0, there are glass including much BaO (barium monoxide) and PbO (lead oxide), hematite (red steel), rutile (gold red stone), germanium, diamond, and silicon. Among them, silicon can be easily obtained as a semiconductor material, and its processing is easy, and its price is relatively cheap. When the thickness of a silicon wafer is processed to 200 μm or less and used as the protection cover, the transmissible property becomes high in a low wavelength region of light, especially, in the near-infrared wavelength region between 800 and 1000 mm, and the sufficient sensor light output is obtained. Also, the silicon is an environment-friendly material as compared with the glass including a harmful substance. Also, the image sensor such as CMOS and CCD is made of a silicon wafer. Therefore, the low portion of the silicon wafer is thinly polished, to have the thickness of 200 μm or less from a photosensitive layer, and then the up and down sides are reversed. Thus, when the lower portion originally serving as the base of the silicon wafer is brought into contact with the skin, the similar structure can be obtained without any special cover.

Figure 17:
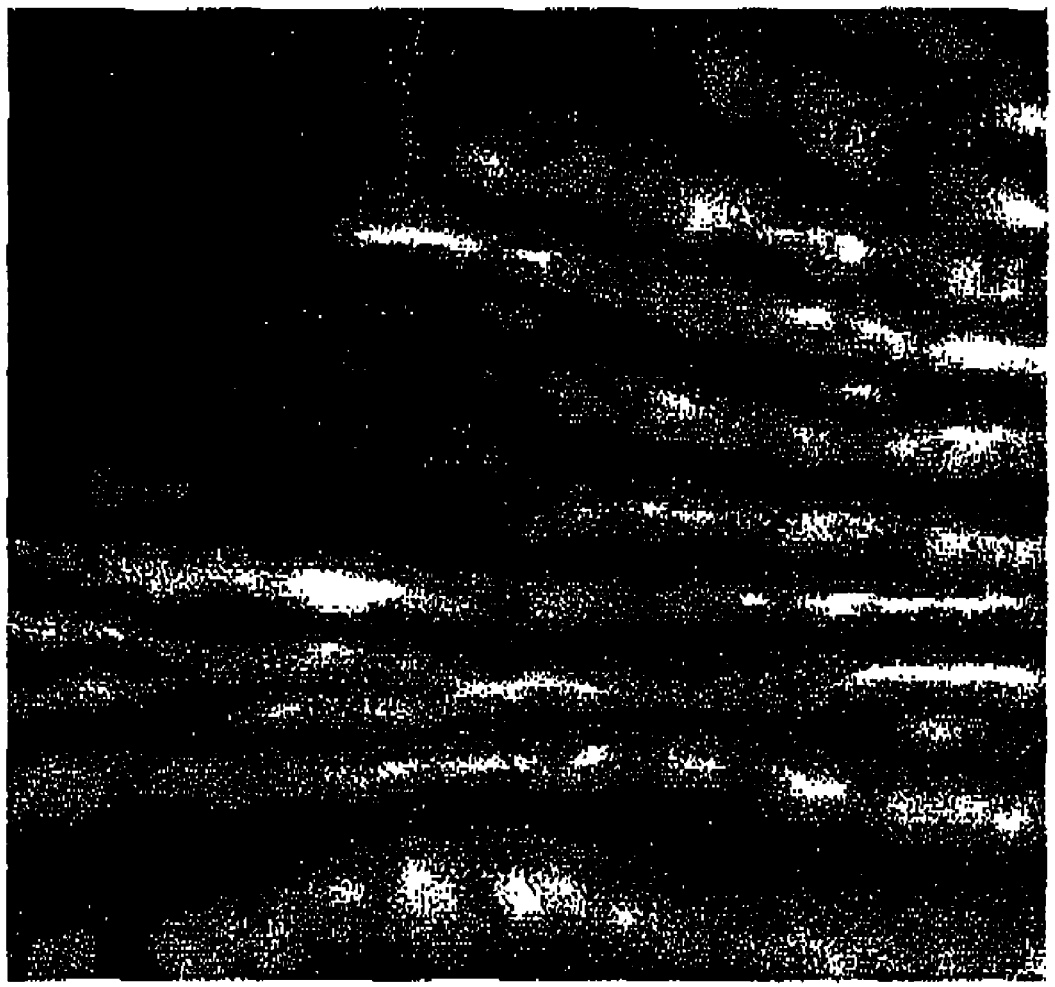
FIG. 17 is a diagram showing a fingerprint image example read by the biometrical feature inputting apparatus according to the third embodiment of the present invention.

FIG. 17 shows the fingerprint image of the finger 4 that is read by the biometrical feature inputting apparatus, in this embodiment having the protection cover 801. The contrast of the ridge section is known to be obtained even in the round skin peeling portion on the upper left part on the image. However, the bright portion and the dark portion are reversed as compared with other location. When the protection cover 801 is installed in this way, the fingerprint ridge section becomes bright, and the valley section becomes dark on the basis of the refractive index of the protection cover 801 as mentioned above and in accordance with the condition of the contact portion. Thus, the relation between the bright and dark portions is reversed as compared with the non-contact portion. This problem can be solved by a method of the imaging process and the fingerprint authentication. That is, only the continuity of the ridge section may be extracted and linked through the edge emphasis. Also, when the authenticating method is based on the positional relation between the feature points such as the branch point and end point of the fingerprint, the reversion of the brightness and darkness relation has no influence on the authentication.

In this way, according to the third embodiment, there is the effect of removing the fear that dust is deposited in the gap 2 of the finger sliding guide 3, so that the image quality is deteriorated, in addition to the attainment of the effect similar to the first embodiment.

Fourth Embodiment

Figure 18:
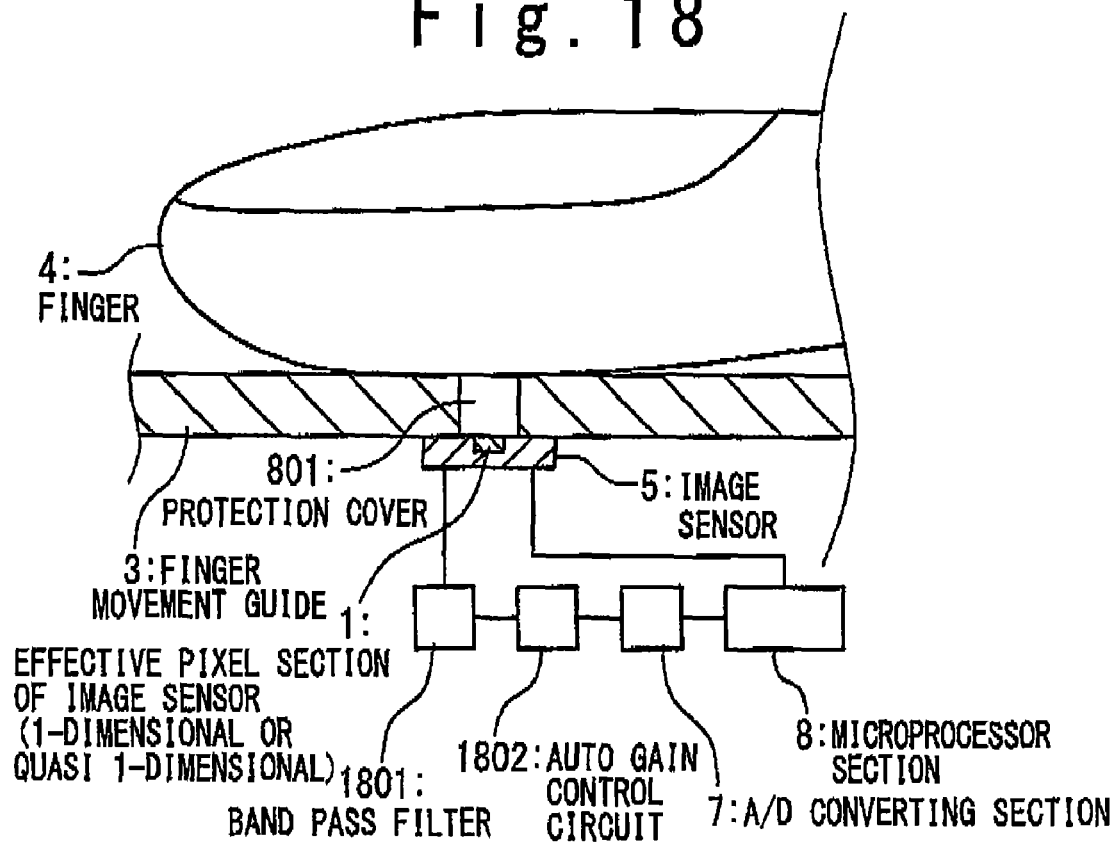
FIG. 18 is a laterally sectional view of the biometrical feature inputting apparatus according to a fourth embodiment of the present invention.

With reference to FIG. 18, the biometrical feature inputting apparatus according to the fourth embodiment of the present invention differs from the third embodiment shown in FIG. 14, in that a band pass filter 1801 and an automatic gain control circuit 1802 are connected between the image sensor 5 and the A/D converter 7, and the components other than them are same as that of the third embodiment.

The band pass filter 1801 extracts only the image component of a fingerprint pitch from the image signal outputted by the image sensor 5. The optimal frequency property of the band pass filter 1801 is determined from the density of the sensors and the scanning frequency by considering the ridge section pitch from 0.2 mm to 0.5 mm. The image component extracted by the band pass filter 1801 is amplified by the automatic gain control circuit 1802 at the later stage and outputted to the A/D converter 7.

According to the fourth embodiment, the band pass filter 1801 for extracting only the image component of the fingerprint pitch from the output of the image sensor 5, and the automatic gain control circuit 1802 for amplifying that output are provided, and even the small output of the skin peeling portion can be amplified. When the material whose refractive index is in the range between 1.4 and 2.0 is used for the protection cover 801, the output of the skin peeling or separation portion becomes excessively small in the third embodiment, so that the recognition becomes difficult. However, the fourth embodiment can improve such problems. If the material such as usual glass having the refractive index between 1.4 and 2.0 is used for the protection cover 801, this is advantage in price. Of course, this embodiment is effective even when the protection cover 801 is made of the material having the refractive index that is outside the range between 1.4 and 2.0.

Fifth Embodiment

Figure 19:
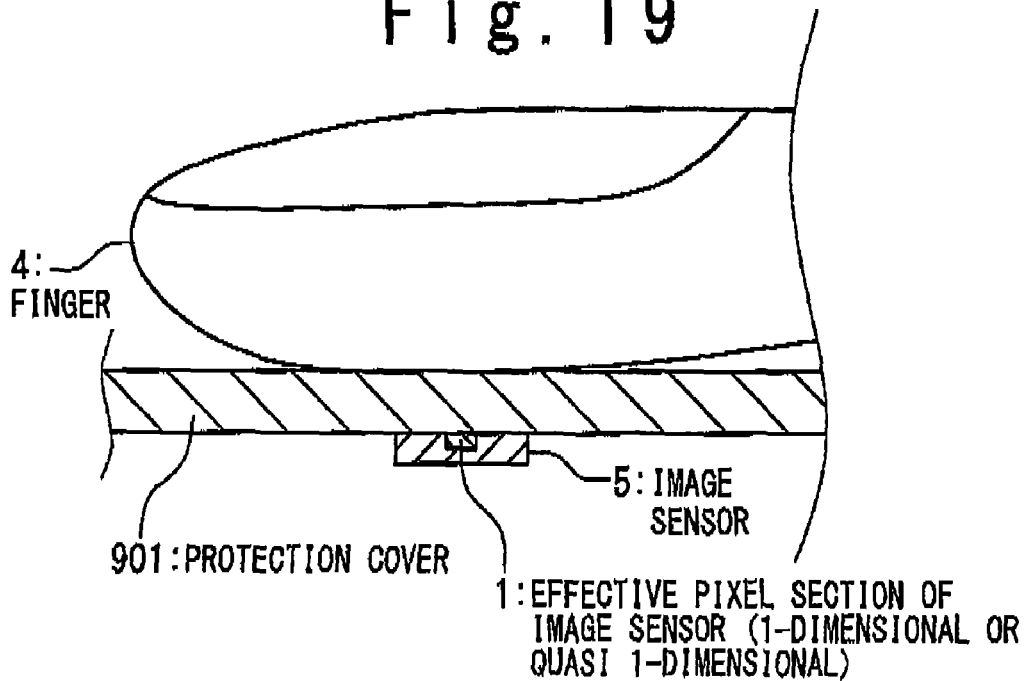
FIG. 19 is a laterally sectional view of the biometrical feature inputting apparatus according to a fifth embodiment of the present invention.

With reference to FIG. 19, the biometrical feature inputting apparatus according to the fifth embodiment of the present invention differs from the third embodiment, in that the entire finger sliding guide 3 is covered with a protection cover 901, and the other components are same as those of the third embodiment.

The protection cover 901 is made of the optically transmissible solid having the refractive index similar to that of the protection cover 801 in the third embodiment, and the condition of its thickness is same as that of the protection cover 801.

According to the fifth embodiment, in addition to the achievement of the similar effect to the third embodiment, the entire finger sliding guide 3 is designed as the protection cover 901. Therefore, the fifth embodiment has the effect that the assembly performance is excellent.

Sixth Embodiment

Figure 20:
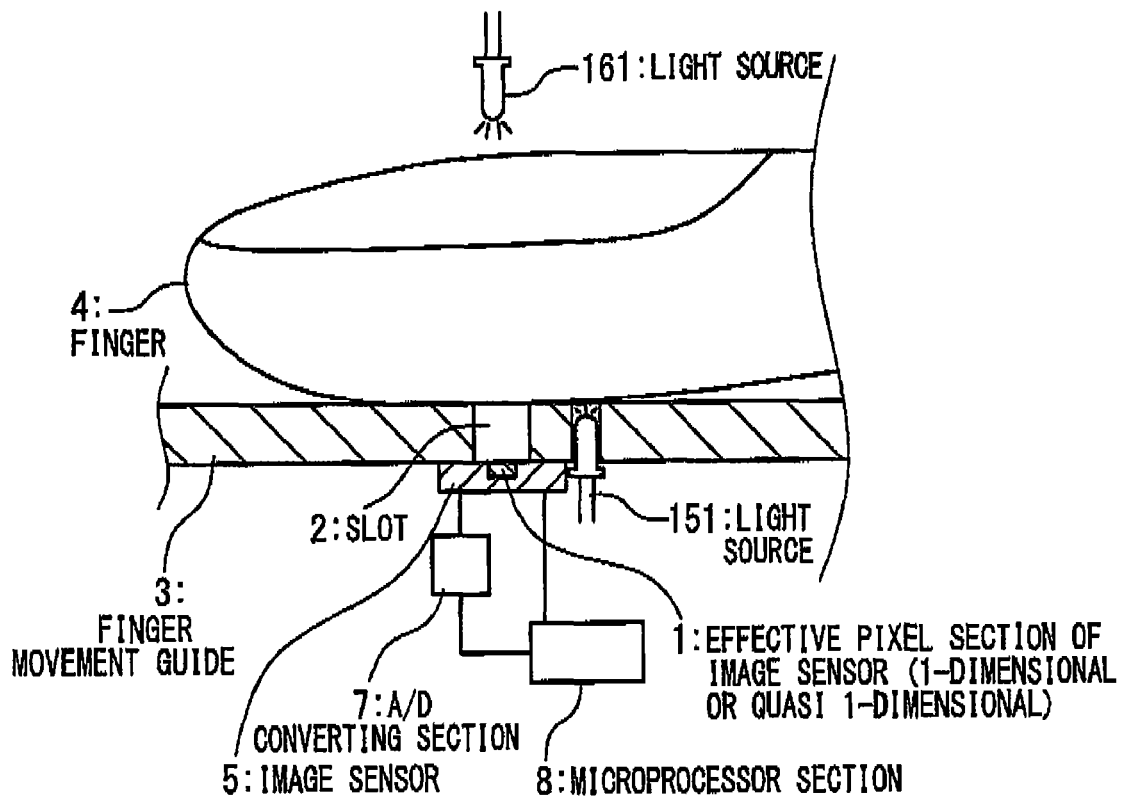
FIG. 20 is a laterally sectional view of the biometrical feature inputting apparatus according to a sixth embodiment of the present invention.

With reference to FIG. 20, the biometrical feature inputting apparatus according to the sixth embodiment differs from the second embodiment, in that the sixth embodiment contains a light source 161 for illuminating the rear portion (nail portion) of the finger 4 from above to read a blood vessel image together with the fingerprint pattern of the finger 4. The other components are same as those of the second embodiment.

The light source 161 is provided above the finger 4 with a support tool (not shown) to read the blood vessel pattern of the finger and emits a light component between about 800 and 1000 nm, which is excellently absorbed by hemoglobin that is higher in the absorption of near-infrared light than the other living body tissues. In particular, LED that is developed for an infrared remote controller to have the wavelength between about 820 and 950 nm has a large output, and is suitable for the light source 161. Only the image on the skin surface can be obtained from the image resulting from the light source 151 placed below the finger 4. However, the image resulting from the light emitted from the upper light source 161 includes the blood vessel image. Since the bloods including hemoglobin passes through thick blood vessels, the blood vessel becomes darker than the other tissues. Thus, the image resulting from the light source 161 and the image resulting from the light source 151 are defined as follows, and the difference between both the images is calculated, which can read the blood vessel pattern together with the fingerprint pattern of the finger.

Figure 21:
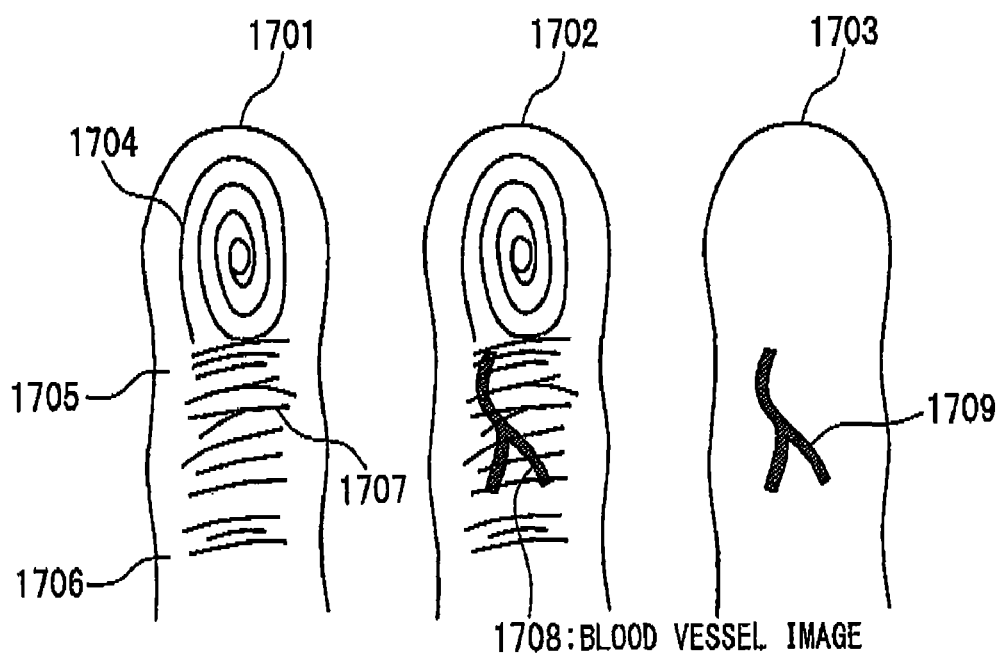
FIG. 21 is a diagram showing a principle when a blood vessel image is read by the biometrical feature inputting apparatus according to the sixth embodiment of the present invention together with a fingerprint image.
Figure 22:
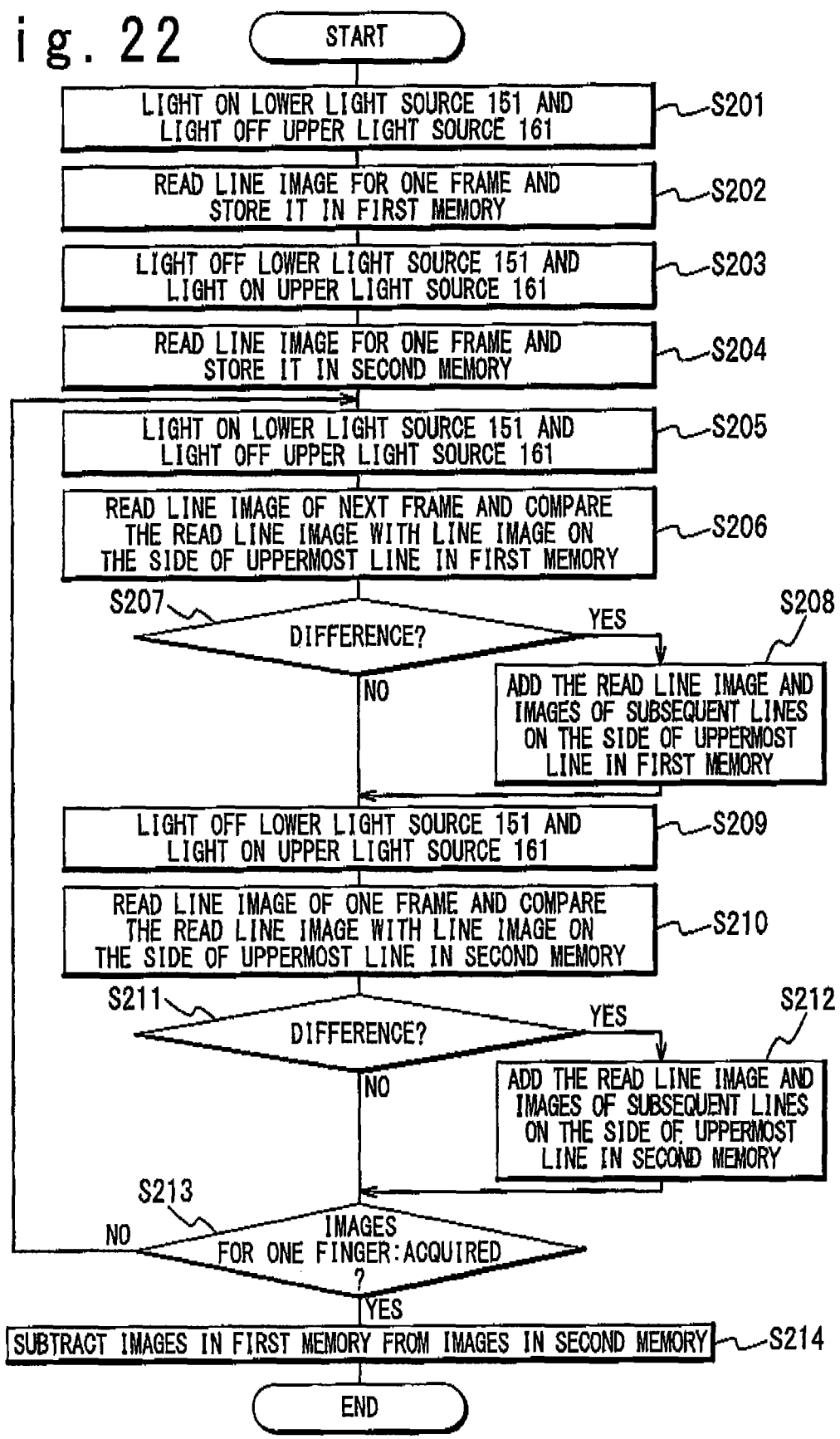
FIG. 22 is a flowchart showing a process example of a microprocessor of the biometrical feature inputting apparatus according to the sixth embodiment of the present invention.

When the biometrical feature inputting apparatus in the sixth embodiment is used to read the blood vessel pattern together with the fingerprint pattern of the finger, the vicinity of the second knuckle of the finger 4 is placed near the gap 2 of the finger sliding guide 3, and the finger 4 is pulled to trace the gap 2 in contact with the cushion of the finger 4. During this movement of the finger 4, the patterns are imaged by the image sensor 5. At first, when the first frame image of the image sensor 5 is obtained, the light source 151 arranged on the lower portion of the finger is turned on to obtain the image. Next, the light source 151 on the lower portion of the finger is turned off, and the light source 161 on the above portion of the finger is turned on to obtain the next frame image of the image sensor 5. This operation is repeated, and the images obtained by using the respective light sources are linked, to obtain an image 1701 resulting from the light source 151 on the lower portion and a image 1702 resulting from the light source 161 on the above portion, as shown in FIG. 21. In both of them, there are a fingerprint 1704 and a pattern 1707 between a first knuckle 1705 and a second knuckle 1707. However, the image obtained by using the upper light source 161 further includes a blood vessel image 1708. By determining the difference between the two images 1701 and 1702 in which they are alternately switched, it is possible to obtain an image 1703 having only a blood vessel image 1709. The process of determining this difference is performed by the microprocessor 8. FIG. 22 shows a processing example.

At first, when only the light source 151 is turned on, a partial image for one frame of the image sensor 5 is read and written into a first memory (not shown) (Steps S201, S202). Next, when only the light source 161 is turned on, a partial image for one frame of the image sensor 5 is read and written into a second memory (not shown) (Steps S203, S204). Next, when only the light source 151 is turned on, a partial image for one frame of the image sensor 5 is read and compared with the image stored in the first memory from the highest line side in units of lines (Steps S205, S206). Then, if there are difference lines from the highest line side of the image stored in the first memory, the different lines are added to the highest line side in the first memory (Steps S207, S208). Next, when only the light source 161 is turned on, the partial image for one frame of the image sensor 5 is read and compared with the image stored in the second memory from the highest line side in units of lines (Steps S209, S210). Then, if there are different lines from the highest line side of the image stored in the second memory, the different lines are added to the highest line side of the partial image stored in the second memory (Steps S211, S212). The processes at the steps S205 to S210 as mentioned above are repeated until the image data corresponding to one finger is obtained (Step S213). Thus, the image 1701 of FIG. 21 is stored in the first memory, and the image 1702 of FIG. 22 is stored in the second memory. Finally, the image stored in the first memory is subtracted from the image stored in the second memory, and the image 1703 of FIG. 21 is generated (Step S214).

In this way, according to the sixth embodiment, since the finger 4 is slid from the second knuckle 1706 to the fingertip on the finger sliding guide 3, the skin pattern 1707 between the first and second knuckles and the blood vessel image 1709 can be read by one operation, together with the fingerprint 1704 of the fingertip. Since the finger is pushed, the blood vessel becomes thin or changed, which results in the insufficient precision as the information of the personal authentication. However, this can be used as the interpolation data for the personal authentication based on the skin pattern such as the fingerprint or can be used to judge the spurious finger. Therefore, this has the effect in which since all of the images are used, the personal authentication can be performed at the precision higher than the single fingerprint of the fingertip.

Seventh Embodiment

The biometrical feature inputting apparatus according to the seventh embodiment of the present invention differs from the first embodiment, in that after the linking process for the partial images by the microprocessor 8, the process for compensating the distortion of the image is performed. The other components are same as those of the first embodiment. Thus, the configuration of the seventh embodiment is same as those shown in FIG. 1.

In the seventh embodiment, the microprocessor 8 performs the process for linking the partial images and the process for performing the distortion compensation for the image in order. The process for linking the partial images is similar to that of the first embodiment. In this case, as the horizontal image of the finger, the uniform image without any distortion at the sensor pitch of the image sensor 5 is obtained. However, the vertical images are distorted because of the movement speed of the finger 4 although the images are linked with an attention. Among the authentication methods by use of the fingerprint, the method in which attention is paid to the relative relation between the branch points and end points of the ridge section is relatively strong against the distortion. However, in order to make the authentication precision higher, the compensation is desired to be performed. In this case, the facts are used that the fingerprint has the ridge components in the horizontal direction and the vertical direction and that a pitch between the ridge sections is substantially constant in the person, and the vertical direction distortion is estimated from the difference of the frequency components between the vertical and horizontal ridge sections. Thus, the compensation will be performed below.

In FIGS. 23A A and 23B, when a frequency component 1202 of a horizontal ridge section in a pattern image 1201 of the original finger is assumed to be f1, a frequency component 1203 in a vertical ridge section is assumed to be f2, and the vertical coordinate of the pixel on the ridge section prior to the compensation is assumed to be Y, a vertical coordinate Y' of the pixel on the ridge section after the compensation is given by the following equation.

$$Y' = Y \times (f2/f1) \tag{1}$$

Figure 25:
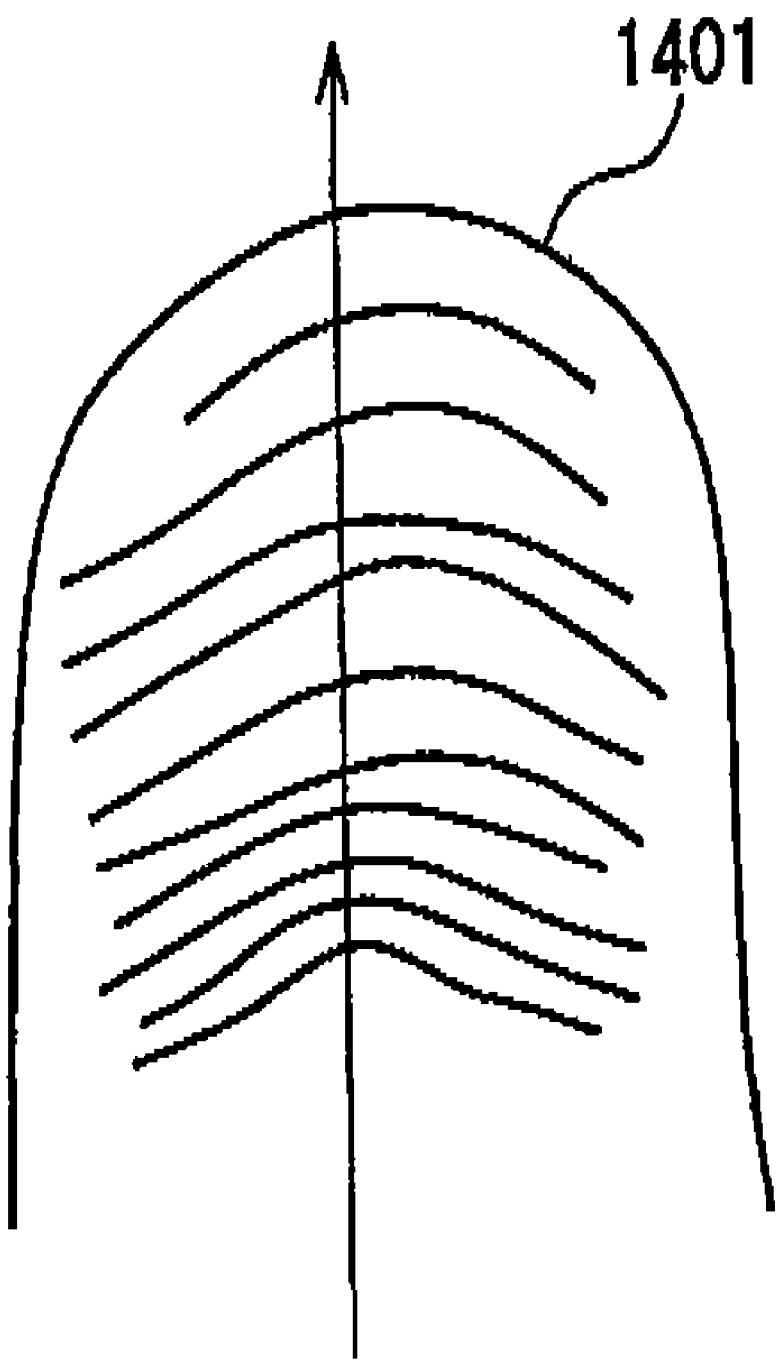
FIG. 25 is a view showing a shape of an arch fingerprint.

FIG. 23A shows a case that the finger is slowly pulled and the image is vertically extended. If the finger is excessively quickly pulled and the image becomes short, although there is a partial loss, a similar image is obtained depending on the lost degree. FIGS. 23A and 23B show a spiral patterns in the fingerprint types, and FIGS. 24A and 24B show a hoof patterns. Statistically, in case of a human, the two patterns are included in many cases. Rarely, there is an arch pattern shown in FIG. 25. In case of this arch pattern, the image component of the horizontal ridge section is greatly different. Thus, the foregoing method cannot be applied. However, since an arch pattern is statistically little (it is said to be 1% or less in case of Japanese), most of the pattern images can be compensated by using the foregoing compensation method.

Figure 26:
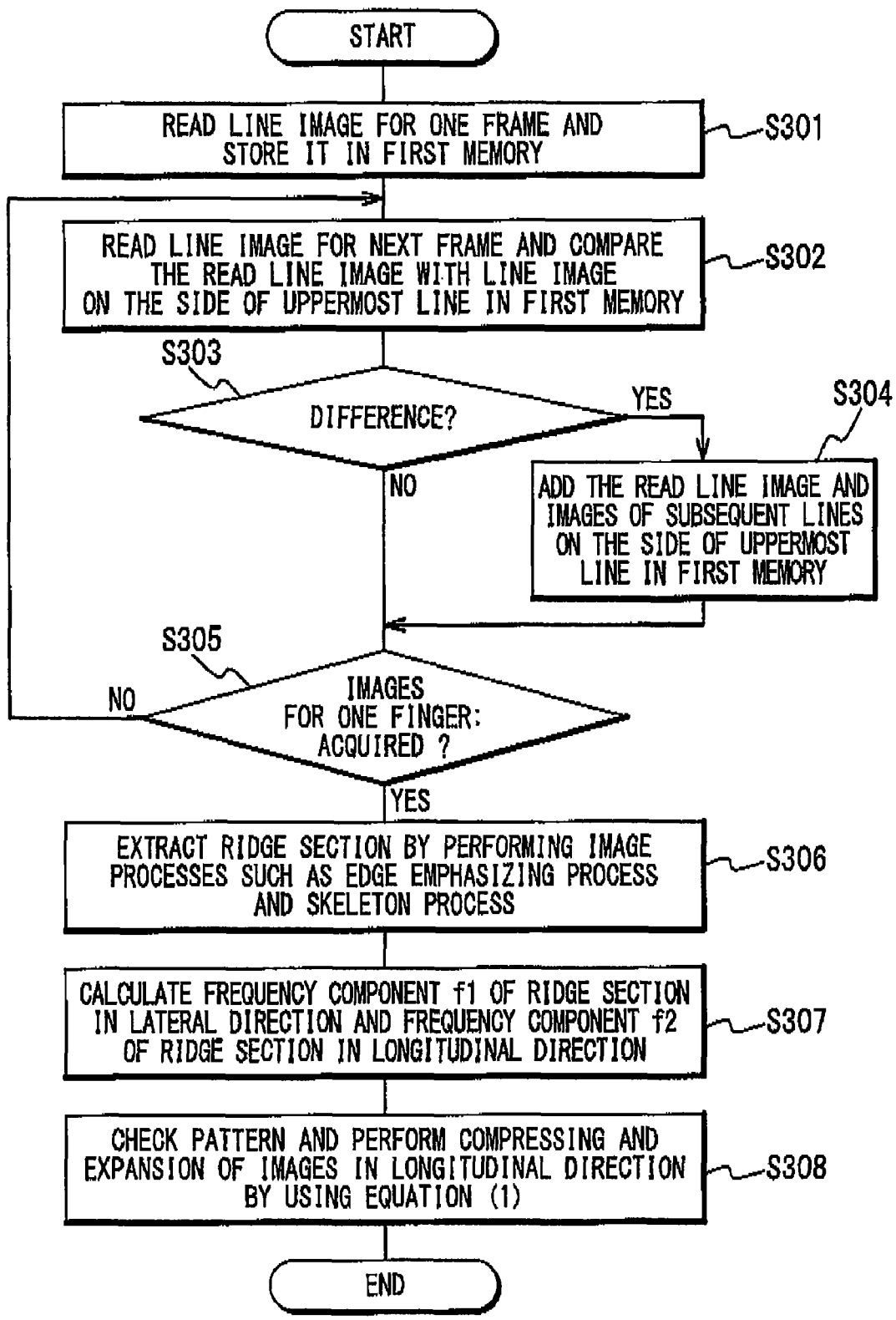
FIG. 26 is a flowchart showing a process example of a microprocessor of the biometrical feature inputting apparatus according to a seventh embodiment of the present invention.

FIG. 26 is a flow chart showing the imaging process performed by the microprocessor 8. Steps S301 to S305 indicate the process of linking the partial images, and they are same as those of the steps S101 to S104 of FIG. 5. The steps S306 to S308 indicate the procedure of the process of compensating a distortion in the image. In the process of compensating the distortion in the image, at first the imaging process such as edge emphasis, skeleton process on the image stored in the first memory is performed to extract the ridge section (Step S306). Next, the numbers of the ridge sections in the horizontal and vertical directions in the image are determined, and the determined numbers are respectively divided by the numbers of pixels in the horizontal and vertical directions. Then, the frequency component f1 of the ridge section in the horizontal direction and the frequency component f2 of the ridge section in the vertical direction are determined (Step S307) Next, a type of the fingerprint pattern is determined from the shape of the ridge section. If the shape of the ridge section is the spiral pattern or the hoof pattern shown in FIGS. 23A and 23B or FIGS. 24A and 25B, the equation (1) is used to compensate the vertical coordinate of the pixel on the ridge section. Thus, the pixel is vertically extended or contracted (Step S308).

In this way, according to the seventh embodiment, it is possible not only to attain only the effect similar to the first embodiment but also to obtain the pattern image whose distortion is little. This is because the vertical distortion in the image is estimated and compensated in accordance with the difference of the image component between the horizontal and vertical ridge sections in the image reconfigured by linking the partial images.

As mentioned above, the present invention has been explained by exemplifying the several embodiments. However, the present invention is not limited to the above-mentioned embodiments. The other various additional modifications can be performed thereon. An embodiment in which the above-mentioned embodiments are properly combined is also considered, such as an embodiment in which the light source 151 in the second embodiment is provided in the third to seventh embodiments and an embodiment in which the band pass filter 1801 and automatic gain control circuit 1802 in the fourth embodiment are installed in the first, third and fifth to seventh embodiments.

As mentioned above, the biometrical feature inputting apparatus according to the present invention is useful as a reading apparatus that stably reads the fingerprint pattern of the finger and the blood vessel pattern and has the small size and the low price. Especially, this is suitable for the apparatus that can input the biometrical feature even under any adverse condition such as the wet or dry state of the finger and the skin separation caused by the dermatitis.

According to the present invention, the biometrical feature such as the fingerprint of the finger can be stably inputted by the image sensor. In Case of the two-dimensional image sensor, it is difficult to stably obtain the fingerprint image while keeping the non-contact state in the constant distance for the finger having the curvature. However, the present invention uses the 1-dimensional or quasi 1-dimensional image sensor and contains the finger sliding guide so that the substantially constant distance is kept without any contact between the finger and the effective pixel unit of the image sensor during the relative motion between the finger and the 1-dimensional or quasi 1-dimensional image sensor.

Also, even under the adverse condition such as the wet or dry state of the finger and the skin separation caused by the dermatitis, the biometrical feature can be inputted. Due to the relative motion between the image sensor and the finger closely placed on the 1-dimensional or quasi 1-dimensional image sensor, while the finger and the image sensor are kept in the non-contact state and the suitable distance so that the image can be directly read, it is possible to read the image of the finger in which the structure inside the finger is reflected. Moreover, this effect will be described by using an actual image example. FIG. 13 shows the image based on the method, that uses the total reflection critical angle, among the conventional methods in which the contact is assumed, and the image is lost on a portion which is located at the substantial center of the image and in which the skin is peeled. FIG. 12 shows an image example of the same portion of the same finger according to the embodiment of the present invention. The contrast is obtained in the portion of the same skin separation. FIG. 17 further shows an image example of the same portion in another embodiment of the present invention. Also in this image, although the bight and dark relation is inverted with regard to the skin peeling portion, the image is obtained without any loss.

Also, it is possible to provide the apparatus that has the small size and the low price and can input the biometrical feature. The method is employed that links the images of the finger in which the structure inside the finger is reflected and this is read while the non-contact state and the suitable distance are kept in which the finger and the image sensor can be directly read by the image, due to the relative motion between the image sensor and the finger closely placed on the 1-dimensional or quasi I-dimensional image sensor. Thus, the parts such as the image sensor are miniaturized, and the low price can be employed.

Also, it is possible to provide the biometrical feature inputting apparatus, which is higher in precision than the conventional biometrical feature inputting apparatus, which is based on only the fingerprint. Since the finger is moved, not only the fingerprint of the fingertip but also the pattern between the first and second knuckles of the finger and the blood vessel image can be inputted to read the many biometrical features at the same time.

As described above, the embodiments of the present invention has been described in detail. However, various changes, variations and modifications without departing from the description in claims and the scope and spirit of the present invention can be understood by those skilled in the art. Also, even if the amendment of the claim is carried out during the examination procedure, the continuation of the inclusion of all equivalents of the claimed invention is the intention of the inventor.

The invention claimed is:

1. A biometrical feature inputting apparatus comprising:
a 1-dimensional or quasi 1-dimensional image sensor;
a finger sliding guide configured to keep a finger not to contact with an effective pixel unit of said image sensor; and
an image processing section configured to link 1-dimensional or quasi 1-dimensional partial images obtained by imaging emission light that is scattered inside the finger and then emitted from a skin surface of the finger by said image sensor during a relative motion, wherein said finger sliding guide has a gap over the effective pixel unit of said image sensor and wherein a height of the gap is 10 gm or more and 200 gm or less, and a length of the gap in a direction of the relative motion is a length of the effective pixel unit or more in a sub scanning direction of said image sensor and 2.0 mm or less.

2. The biometrical feature inputting apparatus according to claim 1, further comprising:
a correcting section configured to correct distortion of the linked images through frequency analysis of a fingerprint portion.

3. An electronic equipment comprising:
a 1-dimensional or quasi 1-dimensional image sensor; and
a finger sliding guide having a gap over an effective pixel unit of said image sensor and configured to keep a finger not to contact with said image sensor, wherein a height of the gap is 10 gm or more and 200 gm or less, and a length of the gap in a direction of a relative motion is a length of the effective pixel unit or more in a sub scanning direction of said image sensor and 2.0 mm or less.

4. The electronic equipment according to claim 3, wherein a height of the gap is 10 µm or more and 200 µm or less.

* * * * *